United States Patent

Aichinger et al.

[11] 3,970,752
[45] July 20, 1976

[54] COCCIDIOCIDAL COMPOSITIONS UTILIZING 1-PHENYL-SUBSTITUTED 1,3,5-TRIAZINE

[75] Inventors: Gerd Aichinger; Axel Haberkorn, both of Wuppertal; Heinrich Kolling, Haan; Eckart Kranz; Josef Reisdorff, both of Wuppertal, all of Germany

[73] Assignee: Bayer Aktiengesellschaft, Germany

[22] Filed: Dec. 12, 1974

[21] Appl. No.: 532,221

Related U.S. Application Data

[62] Division of Ser. No. 452,140, March 18, 1974.

[30] Foreign Application Priority Data

Mar. 20, 1973  Germany............................ 2313721

[52] U.S. Cl. ................................................. 424/249
[51] Int. Cl.². ........................................ A61K 31/53
[58] Field of Search ..................................... 424/249

[56] References Cited
UNITED STATES PATENTS
3,715,356  2/1973  Miller ................................. 424/249

*Primary Examiner*—Sam Rosen

[57] ABSTRACT

1-Phenyl-substituted 1,3,5-triazines of the formula:

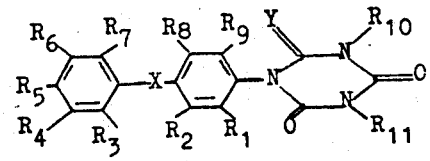

and pharmaceutically acceptable nontoxic salts thereof
wherein $R_1$, $R_2$, $R_3$, $R_4$, $R_5$, $R_6$, $R_7$, $R_8$ and $R_9$ are the same or different and each is selected from the group consisting of hydrogen, straight or branched chain alkyl, haloalkyl, alkoxy, haloalkoxy, alkylthio, haloalkylthio, halogen, nitro, cyano, amino, acylamino, alkoxycarbonylamino, carboxy, alkoxycarbonyl, carbamoyl, acyl, haloacyl, alkylsulphinyl, alkylsulphonyl, haloalkylsulphonyl and sulphamoyl;

$R_{10}$ is hydrogen, straight or branched chain alkyl, cycloalkyl, haloalkyl, alkoxy, alkoxyalkyl, haloalkoxyalkyl, alkylthioalkyl, haloalkylthioalkyl, alkenyl, alkynyl, alkoxycarbonyl, (alkylthio)carbonyl, (alkylthio)thiocarbonyl, acylamino, diacylamino, amino, dialkylamino, polymethyleneimino, polymethyleneimino interrupted by a heteroatom in the chain, or unsubstituted or substituted benzyl or aryl;

$R_{11}$ is hydrogen, or alkyl;

X is sulphur, sulphinyl, or sulphonyl; and

Y is oxygen or sulphur, are useful for their activity against coccidiosis in humans and animals.

43 Claims, No Drawings

COCCIDIOCIDAL COMPOSITIONS UTILIZING 1-PHENYL-SUBSTITUTED 1,3,5-TRIAZINE

This is a division of application Ser. No. 452,140, filed Mar. 18, 1974.

The present invention relates to 1-phenyl-substituted 1,3,5-triazines, processes for their production, pharmaceutical compositions wherein said triazines are the active ingredient, and methods of treating coccidiosis in humans and animals which comprises utilizing said compound as the active agent.

It is known in the art that 2-(4-phenylthio-phenyl)-, 2-(4-phenylsulphinyl-phenyl)- and 2-(4-phenylsulphonyl-phenyl)-1,2,4-triazine-3,5(2H,4H)-diones possess a coccidiostatic action See e.g., Belgian Patent Nos. 740,403 and 773,583 dealing with 2-phenyl-as-triazine-3,5-(2H,4H)-diones and the use of these compounds for combatting coccidiosis.

Those compounds, however, are known only for their activity against poultry coccidiosis and they exhibit only coccidiostatic activity.

More particularly, the present invention is concerned with 1-phenyl-substituted 1,3,5-triazines of the formula:

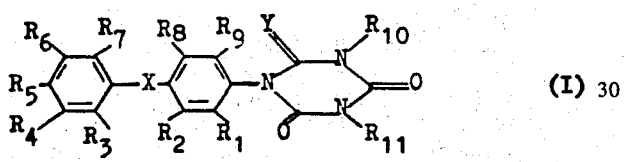

(I)

or pharmaceutically acceptable nontoxic salts thereof wherein
$R_1$, $R_2$, $R_3$, $R_4$, $R_5$, $R_6$, $R_7$, $R_8$ and $R_9$ are the same or different and each is selected from the group consisting of hydrogen, straight or branched chain alkyl, haloalkyl, alkoxy, haloalkoxy, alkylthio, haloalkylthio, halogen, nitro, cyano, amino, acylamino, alkoxycarbonylamino, carboxy, alkoxycarbonyl, carbamoyl, acyl, haloacyl, alkylsulphinyl, alkylsulphonyl, haloalkylsulphonyl and sulphamoyl;

$R_{10}$ is hydrogen, straight or branched chain alkyl, cycloalkyl, haloalkyl, alkoxy, alkoxyalkyl, haloalkoxyalkyl, alkylthioalkyl, haloalkylthioalkyl, alkenyl, alkinyl, alkoxycarbonyl, (alkylthio)carbonyl, (alkylthio)thiocarbonyl, acylamino, diacylamino, amino, dialkylamino, polymethyleneimino, polymethyleneimino interrupted by a heteroatom in the chain, or unsubstituted or substituted benzyl or aryl;

$R_{11}$ is hydrogen, or alkyl;

X is sulphur, sulphinyl, or sulphonyl; and

Y is oxygen or sulphur.

These compounds are active against protozoa and have particular activity against coccidiosis both in humans, mammals generally, and poultry in particular.

The compounds of the present invention may be produced by (a) reacting a compound of the formula:

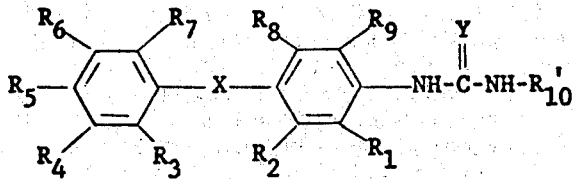

(II)

wherein
$R_1$, $R_2$, $R_3$, $R_4$, $R_5$, $R_6$, $R_7$, $R_8$, $R_9$, X and Y are as above defined; and $R'_{10}$ is hydrogen, straight or branched chain lower alkyl, cycloalkyl of alkyl, to 7 carbon atoms, halo lower alkyl lower alkoxy, lower alkoxy lower alkyl, halo lower alkoxy lower alkyl, lower alkylthio lower alkyl, halo lower alkylthio lower alkyl, lower alkenyl, lower alkinyl, lower alkoxycarbonyl, (lower alkylthio)carbonyl, (lower alkylthio)thiocarbonyl, lower acylamino, dilower acylamino, dilower alkylamino, polymethyleneimino, polymethyleneimino interrupted by a heteroatom, benzyl, monoaryl, or benzyl or monoaryl substituted by halogen, with a carbonylisocyanate of the formula:

(III)

wherein $R_{12}$ is halogen, lower alkoxy, or monoaryloxy, to produce a 1,3,5-triazine of the formula:

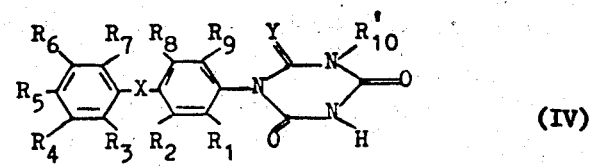

(IV)

wherein
$R_1$, $R_2$, $R_3$, $R_4$, $R_5$, $R_6$, $R_7$, $R_8$, $R_9$, $R'_{10}$, X and Y are as above defined, and if desired reacting said 1,3,5-triazine with an alkylating agent of the formula:

(V)

wherein
A is alkyl;
$n$ is 1, 2 or 3; and
Z is a moiety which easily forms an anion and which together with the acid hydrogen of the imino group of the 1,3,5-triazine forms the moiety $(H)_nZ$ wherein $n$ and Z are as above defined;

(b) converting a compound of the formula:

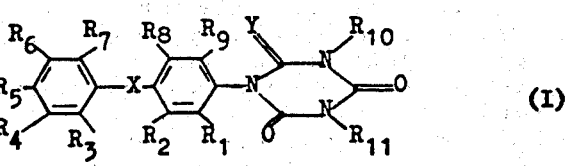

(I)

wherein
$R_1$, $R_2$, $R_3$, $R_4$, $R_5$, $R_6$, $R_7$, $R_8$, $R_9$, $R_{10}$ and $R_{11}$ are as above defined:
X is sulphur; and
Y is oxygen, by reaction with the appropriate amount of an oxidizing agent into a compound of the formula:

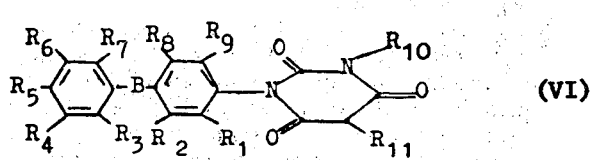

(VI)

wherein
R$_1$, R$_2$, R$_3$, R$_4$, R$_5$, R$_6$, R$_7$, R$_8$, R$_9$, R$_{10}$ and R$_{11}$ are as above defined; and
B is SO or SO$_2$; or (c) converting a compound of the formula:

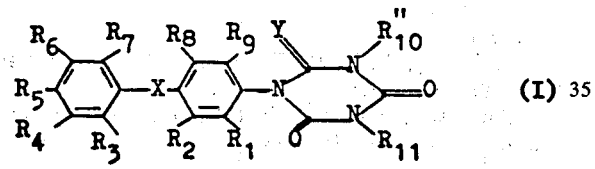

(I)

wherein
R$_1$, R$_2$, R$_3$, R$_4$, R$_5$, R$_6$, R$_7$, R$_8$, R$_9$, R$_{11}$, X and Y are as above defined; and
R''$_{10}$ is acylamino or dilower acylamino.

According to process (c) above, the acyl moiety is split off and compounds of formula I wherein R$_{10}$ is amino are thus produced.

The method by which compounds of formula I, which are used as starting materials according to process (c) above, can specifically be converted into the corresponding amino compounds merely comprises the application of techniques per se known from the literature and thus any suitable conversion method may be utilized.

The compounds of the present invention and their pharmaceutically acceptable nontoxic salts can be interconverted in any suitable manner according to techniques which are per se known.

The compounds of the present invention are particularly useful because they exhibit a far better activity against poultry coccidium *E. tenella* than do commercially available substances which are known such as 3,5-dinitrotoluylamide, 1-[(4-amino-2-propyl-5-pyrimidinyl)-methyl]-2-picolinium chloride hydrochloride, 3,5-dichloro-2,6-dimethylpyridone-4 and the complex obtained from 4,4'-di-(nitrophenyl)urea and 4,6-dimethyl-2-hydroxy-pyrimidine.

In addition, the compounds of the present invention are active as indicated above both against poultry coccidiosis and against mammalian coccidiosis, and thus the compounds of the present invention exhibit a broad spectrum of activity which is not shown by commercially available compounds.

If N-[4-(4'-nitro-phenylthio)-phenyl]-N'-methylurea and chlorocarbonylisocyanate are used as starting substances and methyl iodide is used as the alkylating agent, the course of the reaction can be represented by the following equation:

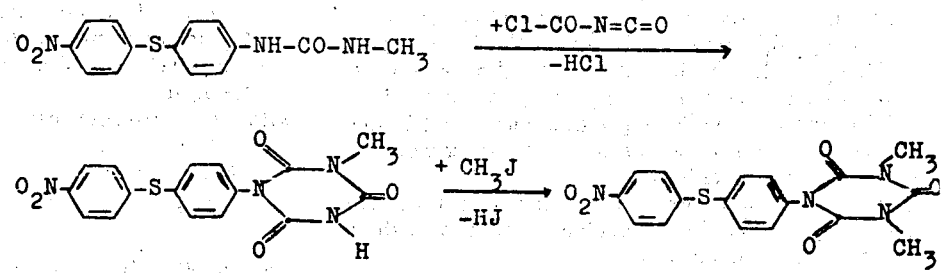

According to one embodiment of the present invention:

R$_1$, R$_2$, R$_3$, R$_4$, R$_5$, R$_6$, R$_7$, R$_8$ and R$_9$ are the same or different and each is selected from the group consisting of hydrogen, straight or branched chain alkyl of 1 to 4 carbon atoms, alkoxy of 1 to 4 carbon atoms, alkylthio of 1 to 4 carbon atoms, trifluoromethyl, chlorine, bromine, nitro, cyano, amino, acylamino of 1 to 4 carbon atoms, alkoxycarbonylamino of 1 to 4 carbon atoms in the alkoxy moiety, carboxy, alkoxycarbonyl of 1 to 4 carbon atoms in the alkoxy moiety, haloalkoxy of 1 to 4 carbon atoms in the alkoxy moiety, haloalkylthio of 1 to 4 carbon atoms in the alkyl moiety, carbamoyl, acyl of 1 to 5 carbon atoms, haloacyl of 1 to 4 carbon atoms, alkylsulphonyl of 1 to 4 carbon atoms, and haloalkylsulphonyl of 1 to 4 carbon atoms;

R$_{10}$ is hydrogen, straight chain alkyl of 1 to 12 carbon atoms, branched chain alkyl of 3 to 5 carbon atoms, ω-chloroalkyl of 1 to 6 carbon atoms, alkoxy of 1 to 6 carbon atoms, alkoxyalkyl of 2 to 6 carbon atoms, haloalkoxyalkyl of 2 to 6 carbon atoms, alkenyl of 2 to 4 carbon atoms, alkynyl of 2 to 4 carbon atoms, alkoxycarbonyl of 1 to 4 carbon atoms, (alkylthio)carbonyl of 1 to 4 carbon atoms, dialkylamino wherein the alkyl groups are the same and each alkyl group is of 1 to 4 carbon atoms, acylamino of 1 to 5 carbon atoms, dilower acylamino, polymethyleneimino, polymethyleneimino interrupted by oxygen, phenyl or halophenyl.

According to another embodiment of the present invention:

R$_1$, R$_2$, R$_3$, R$_4$, R$_5$, R$_6$, R$_7$, R$_8$ and R$_9$ are the same or different and each is selected from the group consisting of hydrogen, alkyl of 1 or 2 carbon atoms, alkoxy of 1 or 2 carbon atoms, alkylthio of 1 or 2 carbon atoms, trifluoromethyl, chlorine, bromine, nitro, cyano, amino, acylamino of 1 or 2 carbon atoms, alkoxycarbonylamino of 1 or 2 carbon atoms, carboxy, alkoxycarbonyl of 1 or 2 carbon atoms, trifluoromethoxy, trifluoromethylthio, carbamoyl, acyl of 1 or 2 carbon atoms, trifluoroacetyl, alkylsulphonyl of 1 or 2 carbon atoms, and trifluoromethylsulphonyl; and $R_{10}$ is hydrogen, alkyl of 1 to 4 carbon atoms, alkoxy of 1 or 2 carbon atoms, alkoxyalkyl of 2 to 4 carbon atoms, trifluoromethoxymethyl, alkinyl of 2 or 3 carbon atoms, alkoxycarbonyl of 1 to 2 carbon atoms, (alkylthio)carbonyl of 1 or 2 carbon atoms, dimethylamino, diethylamino, phthalimido, succinimido, phenyl, chlorophenyl, or bromophenyl.

According to another embodiment of the present invention:

$R_1$, $R_2$, $R_3$, $R_4$, $R_5$, $R_6$, $R_7$, $R_8$ and $R_9$ are the same or different and each is selected from the group consisting of hydrogen, alkyl of 1 or 2 carbon atoms, alkoxy of 1 or 2 carbon atoms, chlorine, bromine, nitro, cyano, trifluoromethyl, alkoxycarbonylamino of 1 or 2 carbon atoms, acylamino of 1 or 2 carbon atoms, alkylsulphonyl of 1 or 2 carbon atoms and trifluoromethylsulphonyl;

$R_{10}$ is alkyl of 1 to 4 carbon atoms, amino or phthalimido; and $R_{11}$ is hydrogen.

According to another embodiment of the present invention:

Y is oxygen.

According to another embodiment of the present invention:

$R_1$, $R_4$, $R_9$ and $R_{11}$ are each hydrogen;

$R_2$ is hydrogen, alkyl of 1 or 2 carbon atoms, chlorine or bromine;

$R_3$ is hydrogen, alkyl of 1 or 2 carbon atoms, alkoxy of 1 or 2 carbon atoms, chlorine or bromine;

$R_5$ is alkyl of 1 or 2 carbon atoms, chlorine, bromine, nitro, cyano, trifluoromethyl, alkoxy, carbonylamino of 1 or 2 carbon atoms, acylamino of 1 or 2 carbon atoms, alkylsulphonyl of 1 or 2 carbon atoms, or trifluoromethylsulphonyl;

$R_6$ is hydrogen, alkyl of 1 or 2 carbon atoms, chlorine, or bromine;

$R_7$ is hydrogen or alkyl of 1 or 2 carbon atoms;

$R_8$ is hydrogen, alkyl of 1 or 2 carbon atoms, chlorine, or bromine;

$R_{10}$ is alkyl of 1 to 4 carbon atoms, amino, or phthalimido; and

Y is oxygen.

According to another embodiment of the present invention:

$R_1$ is hydrogen;

$R_2$ is hydrogen, methyl, or chlorine;

$R_3$ is hydrogen, methyl, methoxy, or chlorine;

$R_4$ is hydrogen;

$R_5$ is methyl, chlorine, nitro, cyano, trifluoromethyl, ethoxycarbonylamino, acetamido, methylsulphonyl, or trifluoromethylsulphonyl;

$R_6$ is hydrogen, methyl, or chlorine;

$R_7$ is hydrogen, or methyl;

$R_8$ is hydrogen, methyl, or chlorine;

$R_9$ is hydrogen;

$R_{10}$ is methyl, ethyl, propyl, butyl, amino, or phthalimido;

$R_{11}$ is hydrogen; and

Y is oxygen.

According to another embodiment of the present invention:

$R_1$, $R_2$, $R_3$, $R_4$, $R_5$, $R_6$, $R_7$, $R_8$ and $R_9$ are the same or different and each is selected from the group consisting of hydrogen, alkyl of 1 to 4 carbon atoms, alkoxy of 1 or 2 carbon atoms, chlorine, bromine, nitro, cyano, trifluoromethyl, trifluoromethoxy, acylamino of 1 or 2 carbon atoms, alkoxycarbonylamino of 1 or 2 carbon atoms, acyl of 1 or 2 carbon atoms, or alkylsulphonyl of 1 or 2 carbon atoms;

$R_{10}$ is hydrogen, straight or branched chain alkyl of 1 to 4 carbon atoms, alkenyl of 2 or 3 carbon atoms, alkoxyalkyl of 2 to 5 carbon atoms, alkoxy of 1 or 2 carbon atoms, or phthalimido; and $R_{11}$ is hydrogen, or alkyl of 1 to 3 carbon atoms.

According to another embodiment of the present invention:

$R_1$ is hydrogen, or alkyl of 1 or 2 carbon atoms;

$R_2$ is hydrogen, alkyl of 1 or 2 carbon atoms, chlorine, or bromine;

$R_3$ is hydrogen, alkyl of 1 or 2 carbon atoms, alkoxy of 1 or 2 carbon atoms, chlorine, or bromine;

$R_4$ is hydrogen, alkoxy of 1 or 2 carbon atoms, or cyano;

$R_5$ is hydrogen, straight or branched chain alkyl of 1 to 4 carbon atoms, chlorine, bromine, nitro, cyano, trifluoromethyl, trifluoromethoxy, acylamino of 1 or 2 carbon atoms, alkoxycarbonyl of 1 or 2 carbon atoms, acyl of 1 or 2 carbon atoms, or alkylsulphonyl of 1 or 2 carbon atoms;

$R_6$ is hydrogen, alkyl of 1 or 2 carbon atoms, alkoxy of 1 or 2 carbon atoms, chlorine, bromine, or trifluoromethyl;

$R_7$ is hydrogen, alkyl of 1 or 2 carbon atoms, alkoxy of 1 or 2 carbon atoms, chlorine, or bromine;

$R_8$ is hydrogen, alkyl of 1 or 2 carbon atoms, chlorine, or bromine;

$R_9$ is hydrogen;

$R_{10}$ is hydrogen, straight or branched chain alkyl of 1 to 4 carbon atoms, alkenyl of 2 or 3 carbon atoms, alkoxyalkyl of 2 to 5 carbon atoms, alkoxy of 1 to 2 carbon atoms, or phthalimido; and $R_{11}$ is hydrogen, or alkyl of 1 to 3 carbon atoms.

According to another embodiment of the present invention:

$R_1$ is hydrogen, or methyl;

$R_2$ is hydrogen, methyl, or chlorine;

$R_3$ is hydrogen, methyl, ethyl, methoxy, or chlorine;

$R_4$ is hydrogen, ethoxy, or cyano;

$R_5$ is hydrogen, methyl, tert.-butyl, chlorine, bromine, nitro, cyano, trifluoromethyl, trifluoromethoxy, acetamido, ethoxycarbonylamino, acetyl, or methylsulphonyl;

$R_6$ is hydrogen, methyl, methoxy, chlorine, or trifluoromethyl;

$R_7$ is hydrogen, methyl, methoxy, or chlorine;

$R_8$ is hydrogen, methyl, or chlorine;

$R_9$ is hydrogen;

$R_{10}$ is hydrogen, methyl, ethyl, n-propyl, i-propyl, tert-butyl, allyl, methoxyethyl, methoxypropyl, ethoxypropyl, methoxy, ethoxy, or phthalimino; and $R_{11}$ is hydrogen, or propyl.

$R_{12}$ is preferably chlorine, methoxy or phenoxy;

Z is preferably halogen, especially chlorine, bromine or iodine, or $SO_4$; and

A is preferably alkyl of 1 to 4 carbon atoms.

According to the process above set forth, $R'_{10}$ is preferably hydrogen, straight chain alkyl of 1 to 12 carbon atoms, branched chain alkyl of 3 to 5 carbon atoms, ω-chloroalkyl of 1 to 6 carbon atoms, alkoxy of 1 to 6 carbon atoms, alkoxyalkyl of 2 to 6 carbon atoms, haloalkoxyalkyl of 2 to 6 carbon atoms, alkenyl of 2 to 4 carbon atoms, alkinyl of 2 to 4 carbon atoms, alkoxycarbonyl of 1 to 4 carbon atoms, (alkylthio)carbonyl of 1 to 4 carbon atoms, dialkylamino wherein the alkyl groups are the same and each alkyl group is of 1 to 4 carbon atoms, acylamino of 1 to 5 carbon atoms, dilower acylamino, polymethyleneimino, polymethyleneimino interrupted by oxygen, phenyl, or halophenyl.

According to another embodiment of the above described process, $R'_{10}$ is hydrogen, alkyl of 1 to 4 carbon atoms, alkoxy of 1 or 2 carbon atoms, alkoxyalkyl of 2 to 4 carbon atoms, trifluoromethoxymethyl, alkenyl of 2 or 3 carbon atoms, alkoxycarbonyl of 1 or 2 carbon atoms, (alkylthio)carbonyl of 1 or 2 carbon atoms, dimethylamino, diethylamino, phthalimido, succinimido, phenyl, chlorophenyl or bromophenyl.

According to another embodiment of the above described process, $R'_{10}$ is alkyl of 1 to 4 carbon atoms, or phthalimido.

According to another embodiment of the above described process, $R'_{10}$ is methyl, ethyl, propyl, butyl, or phthalimido.

According to another embodiment of the above described process, $R'_{10}$ is hydrogen, straight or branched chain alkyl of 1 to 4 carbon atoms, alkenyl of 2 to 3 carbon atoms, alkoxyalkyl of 2 to 5 carbon atoms, alkoxy of 1 or 2 carbon atoms, or phthalimido.

According to another embodiment of the above described process, $R'_{10}$ is hydrogen, methyl, ethyl, n-propyl, i-propyl, tert.-butyl, allyl, methoxyethyl, methoxypropyl, ethoxypropyl, methoxy, ethoxy, or phthalimido.

According to another embodiment of the above described process, when $R''_{10}$ is acylamino, it is preferably lower acylamino, especially acylamino of 1 to 4 carbon atoms and particularly of 1 to 2 carbon atoms.

The substituted ureas or thioureas of the formula II above which are used as starting materials for producing the compounds of the present invention are not per se known but can be prepared according to techniques which are themselves per se known by either:

a. reacting substituted 4-aminodiphenyl-thioethers, -sulphoxides or -sulphones with the appropriate substituted isocyanates or isothiocyanates in inert organic solvents, if necessary in the presence of tertiary bases such as triethylamine, pyridine or several others, at temperatures between 0°C and 100°C; or, reversing the sequence, by b. reacting substituted amines with the appropriately substituted 4-isocyanato- or 4-isothiocyanato-diphenyl-thioethers, -sulphoxides or -sulphones under the same conditions.

If the amount of solvent is suitably chosen, the reaction products as a rule crystallize out on cooling the solution. Details of the preparation of ureas by interaction of amines and isocyanates are to be found in "Methoden der Org. Chemie" (Methods of Organic Chemistry) (Houben-Weyl), 4th edition, volume VIII, pages 157–158.

Representative compounds of formula II above which may be used according to the process of the present invention include:

N-[4-(2',4',6'-trimethyl-phenylthio)-phenyl]-N'-methyl-urea,
N-[4-(2',4'-dichloro-phenylthio)-3,5-dimethyl-phenyl]-N'-methyl-urea,
N-[3,5-dichloro-4-(2'-chloro-4'-trifluoromethyl-phenylthio)-phenyl]-N'-ethyl-urea,
N-[3,5-dichloro-4-(4'-methylsulphonyl-phenylthio)-phenyl]-N'-methyl-urea,
N-[4-(4'-trifluoromethylsulphonyl-phenylthio)-phenyl]-N'-ethyl-urea,
N-[3,5-dichloro-4(4'-trifluoromethylsulphonyl-phenylthio)-phenyl]-N'-methyl-urea,
N-[4-(4'-chloro-phenylsulphinyl)-phenyl]-N'-methyl-urea,
N-[4-(4'-chloro-phenylsulphinyl)-phenyl]-N'-ethyl-urea,
N-[4-(4'-chloro-phenylsulphinyl)-phenyl]-N'-propyl-urea,
N-[4-(5'-chloro-2'-methoxy-phenylsulphinyl)-3,5-dimethylphenyl]-N'-ethyl-urea,
N-[3,5-dichloro-4-(5'-chloro-2'-methyl-phenylsulphinyl)-phenyl]-N'-methyl-urea,
N-[3,5-dichloro-4-(2'-methoxy-5'-methyl-phenylsulphinyl)-phenyl]-N'-methyl-urea,
N-[3-chloro-4-(4'-chloro-phenylsulphinyl)-5-methyl-phenyl]-N'-ethyl-urea,
N-[4-(2'-chloro-6'-methyl-4'-nitro-phenylsulphinyl)-phenyl]-N'-ethyl-urea,
N-[4-(4'-methyl-phenylsulphinyl)-phenyl]-N'-ethyl-urea,
N-[4-(4'-nitro-phenylsulphinyl)-phenyl]-N'-propyl-urea,
N-[3,5-dichloro-4-(5'-chloro-2'-methoxy-phenylsulphonyl)-phenyl]-N'-methyl-urea,
N-[4-(5'-chloro-2'-methoxy-phenylsulphonyl)-3,5-dimethylphenyl]-N'-ethyl-urea,
N-[3,5-dichloro-4-(5'-chloro-2'-methyl-phenylsulphonyl)-phenyl]-N'-methyl-urea,
N-[3,5-dichloro-4-(2'-methoxy-5'-methyl-phenylsulphonyl)-phenyl]-N'-methyl-urea,
N-[4-(2'-chloro-6'-methyl-4'-nitro-phenylsulphonyl)-phenyl]-N'-ethyl-urea,
N-[3-chloro-4-(4'-chloro-phenylsulphonyl)-5-methyl-phenyl]-N'-ethyl-urea,
N-[4-(4'-nitro-phenylsulphinyl)-phenyl]-N'-phthalimido-urea,
N-[4-(4'-nitro-phenylsulphonyl)-phenyl]-N'-phthalimido-urea,
N-[3,5-dichloro-4-(4'-trifluoromethyl-phenylsulphonyl)-phenyl]-N'-methyl-urea,
N-[4-(4'-trifluoromethylsulphonyl-phenylsulphonyl)-phenyl]-N'-ethyl-urea,
N-[3,5-dichloro-4-(4'-trifluoromethylsulphonyl-phenylsulphonyl)-phenyl]-N'-methyl-urea and
N-[4-(4'-acetamido-phenylthio)-phenyl]-N'-ethyl-urea.

As diluents in process (a) and in process (b) according to the invention it is possible to use any organic solvents which are inert towards this reaction. These include, in addition to pyridine, preferably aromatic hydrocarbons such as benzene, toluene or xylene, halogenated aromatic hydrocarbons such as chlorobenzene and dichlorobenzene, and ethers such as tetrahydrofurane and dioxane.

The hydrochloric acid produced in the reaction (a) (if $R_{12}$ = Cl) is evolved as a gas or can be bound by organic or inorganic acid acceptors. Preferred acid acceptors include tertiary organic bases such as triethylamine, pyridine, and inorganic bases such as alkali metal carbonates or alkaline earth metal carbonates.

For both the above mentioned reaction steps, the reaction temperatures can be varied within a substantial range. In general, the reaction is carried out at between about 0°C and about 150°C, preferably between 20°C and 100°C.

According to the above reactions, the pressure is generally atmospheric but elevated pressure may also be used. Atmospheric pressure is generally used however.

In carrying out the process according to the invention, the substances participating in the reaction are employed in molar amounts.

The following can optionally be employed as oxidizing agents in process (b): $H_2O_2$/glacial acetic acid, $H_2O_2$/acetic anhydride, per-acids (for example, m-chloroperbenzoic acid), chromic acid and potassium permanganate.

The following compounds are representative of those of the present invention:

1-[4-(4'-ethoxycarbonylamino-phenylthio)-phenyl]-3-methyl-1,3,5-triazine-2,4,6(1H,3H,5H)-trione, melting point 231°C, 1-[4-(4'-nitro-phenylthio)-phenyl]-3-methyl-1,3,5-triazine-2,4,6-(1H,3H,5H)-trione, melting point 194°C, 1-[4-(4'-nitro-phenylthio)-phenyl]-3-ethyl-1,3,5-triazine-2,4,6(1H,3H,5H)-trione, melting point 210°C, 1-[4-(4'-nitro-phenylthio)-phenyl]-3-propyl-1,3,5-triazine-2,4,6(1H,3H,5H)-trione, melting point 226°C, 1-[4-(4'-cyano-phenylthio)-phenyl]-3-methyl-1,3,5-triazine-2,4,6(1H,3H,5H)-trione, melting point 207°C, 1-[4-(4'-nitro-phenylthio)-phenyl]-3-butyl-1,3,5-triazine-2,4,6(1H,3H,5H)-trione, melting point 195°C, 1-[4-(4'-chloro-phenylsulphonyl)-phenyl]-3-methyl-1,3,5-triazine-2,4,6(1H,3H,5H)-trione, melting point 251°C, 1-[4-(4'-acetamido-phenylthio)-phenyl]-3-ethyl-1,3,5triazine-2,4,6(1H,3H,5H)-trione, 1-[4-(2',4',6'-trimethyl-phenylthio)-phenyl]-3-methyl-1,3,5-triazine-2,4,6(1H,3H,5H)-trione, 1-[4-(2',4'-dichloro-phenylthio)-3,5-dimethyl-phenyl]-3-methyl-1,3,5-triazine-2,4,6(1H,3H,5H)-trione, 1-[3,5-dichloro-4-(2'-chloro-4'-trifluoromethyl-phenylthio)-phenyl]-3-ethyl-1,3,5-triazine-2,4,6(1H,3H,5H)-trione, 1-[3,5-dichloro-4-(2'-chloro-6'-methyl-4'-nitro-phenylthio)-phenyl]-3-ethyl-1,3,5-triazine-2,4,6(1H,3H,5H)-trione, melting point 259°C, 1-[4-(4'-nitro-phenylthio)-phenyl]-3-amino-1,3,5-triazine-2,4,6(1H,3H,5H)-trione, 1-[4-(4'-nitro-phenylsulphinyl-phenyl]-3-phthalimido-1,3,5-triazine-2,4,6(1H,3H,5H)-trione, 1-[3,5-dichloro-4-(4'-methylsulphonyl-phenylthio)-phenyl]-3-methyl-1,3,5-triazine-2,4,6(1H,3H,5H)-trione, 1-[4-(4'-trifluoromethylsulphonyl-phenylthio)-phenyl]-3-ethyl-1,3,5-triazine-2,4,6(1H,3H,5H)-trione, melting point 209°C, 1-[3,5-dichloro-4-(4'-trifluoromethylsulphonyl-phenylthio)-phenyl]-3-methyl-1,3,5-triazine-2,4,6(1H,3H,5H)-trione, 1-[4-(4'-chloro-phenylsulphinyl)-phenyl]-3-methyl-1,3,5-triazine-2,4,6(1H,3H,5H)-trione, melting point 258°C, 1-[4-(4'-chloro-phenylsulphinyl)-phenyl]-3-propyl-1,3,5-triazine-2,4,6(1H,3H,5H)-trione, 1-[4-(5'-chloro-2'-methoxy-phenylsulphinyl)-3,5-dimethylphenyl]-3-ethyl-1,3,5-triazine-2,4,6(1H,3H,5H)-trione, 1-[3,5-dichloro-4-(5'-chloro-2'-methyl-phenylsulphinyl)-phenyl]-3-methyl-1,3,5-triazine-2,4,6(1H,3H,5H)-trione, 1-[3,5-dichloro-4-(2'-methoxy-5'-methyl-phenylsulphinyl)-phenyl]-3-methyl-1,3,5-triazine-2,4,6(1H,3H,5H)-trione, 1-[3-chloro-4-(4'-chloro-phenylsulphinyl)-5-methyl-phenyl]-3-ethyl-1,3,5-triazine-2,4,6(1H,3H,5H)-trione, 1-[4-(2'-chloro-6'-methyl-4'-nitro-phenylsulphinyl)-phenyl]-3-ethyl-1,3,5-triazine-2,4,6(1H,3H,5H)-trione, 1-[4-(4'-nitro-phenylsulphinyl)-phenyl]-3-amino-1,3,5-triazine-2,4,6(1H,3H,5H)-trione, 1-[4-(4'-ethoxycarbonylamino-phenylsulphinyl)-phenyl]-3-methyl-1,3,5-triazine-2,4,6(1H,3H,5H)-trione, 1-[4-(4'-methyl-phenylsulphinyl)-phenyl]-3-ethyl-1,3,5-triazine-2,4,6(1H,3H,5H)-trione, 1-[3,5-dichloro-4-(5'-chloro-2'-methyl-phenylsulphonyl)-phenyl]-3-methyl-1,3,5-triazine-2,4,6(1H,3H,5H)-trione, 1-[3-chloro-4-(4'-chloro-phenylsulphonyl)-5-methyl-phenyl]-3-ethyl-1,3,5-triazine-2,4,6(1H,3H,5H)-trione, melting point 198°C, 1-[4-(4'-nitro-phenylsulphonyl)-phenyl]-3-phthalimido-1,3,5-triazine-2,4,6(1H,3H,5H)-trione, 1-[4-(4'-ethoxycarbonylamino-phenylsulphonyl)-phenyl]-3-methyl-1,3,5-triazine-2,4,6(1H,3H,5H)-trione, 1-[4-(4'-trifluoromethylsulphonyl-phenylsulphonyl)-phenyl]-3-ethyl-1,3,5-triazine-2,4,6(1H,3H,5H)-trione, 1-[3,5-dichloro-4-(4'-trifluoromethylsulphonyl-phenylsulphonyl)-phenyl]-3-methyl-1,3,5-triazine-2,4,6(1H,3H,5H)-trione, 1-[4-(4'-nitro-phenylthio)-phenyl]-3-amino-1,3,5-triazine-2,4,6(1H,3H,5H)-trione, 1-[4-(4'-nitro-phenylsulphinyl)-phenyl]-3-amino-1,3,5-triazine-2,4,6(1H,3H,5H)-trione and 1-[4-(4'-nitro-phenylsulphonyl)-phenyl]-3-amino-1,3,5-triazine-2,4,6(1H,3H,5H)-trione.

The compounds of the present invention and their pharmaceutically acceptable nontoxic salts exhibit good activity against varieties of coccidia in poultry such as, for example, *Eimeria tenella* (appendicecal coccidiosis in chickens), *E. acervulina, E. brunetti, E. maxima, E. mitis, E. mivati, E. necatrix* and *E. praecox* (coccidiosis of the small intestine in chickens). The preparation can furthermore be employed for the prophylaxis and treatment of coccidiosis infections of other types of domestic poultry. In addition, the compounds of the present invention exhibit a strong activity in coccidial infections of mammals, such as, for example, of rabbits (*E. stiedae*/liver coccidiosis, *E. magna, E. media, E. irresidua* and *E. perforans*/intestinal coccidiosis), of sheep, cattle and other domestic animals, including dogs and cats, and of laboratory animals such as white mice (*E. falciformis*) and rats.

Furthermore, an activity against toxoplasmosis was found. In treatment or prophylaxis of this infection, the compounds can be employed both for the treatment of the cats which may be responsible for excretion in the infectious stages (oocysts) and for the treatment of the infected humans. Coccidial infections can lead to heavy losses among domestic animals and represent a real problem in raising poultry and mammals such as cattle, sheep, rabbits and dogs. The effect of the known agents against coccidiosis are in most cases restricted to a few species of poultry. The treatment and prophylaxis of mammal coccidiosis hitherto represents a largely unsolved problem.

The pharmaceutical compositions of the present invention contain a major or minor amount e.g. 0.1% to 99.5%, preferably 0.5% to 90% of at least one 1-phenyl-substituted 1,3,5-triazine as above defined in combination with a pharmaceutically acceptable nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and-/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effective utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is 250 mg. to 25 g. of active ingredient.

While the routes of administration include oral, parenteral (i.e. intramuscular, intraperitoneal, and intravenous), rectal and topical, oral administration is particularly preferred.

The present invention also comprises a feedstuff which comprises 25 to 5,000, preferably 50 to 250, ppm of a compound according to the present invention in combination with a suitable edible material, for example, with the chick feedstuff described in the following formulation:

52.000% of shredded fodder grain
17.990% of shredded soya
5.000% of maize gluten feedstuff
5.000% of wheat wholemeal
3.000% of fishmeal
3.000% of tapioca meal
3.000% of green lucerne meal
2.000% of comminuted wheatgerm
2.000% of soya oil
1.600% of fish bonemeal
1.500% of whey powder
1.400% of calcium carbonate for feedstuffs
1.000% of calcium phosphate for feedstuffs
1.000% of molasses
0.500% of brewer's yeast
0.010% of 1-[4-(4'-nitro-phenylthio)-phenyl]-3-propyl 1,3,5-triazine-2,4,6(1H,3H,5H)-trione
100.000%

Such a feedstuff can be used both for curative and for prophylactic purposes.

The present invention also includes a concentrate or a premix which would comprise 1 to 30%, preferably 10 to 20%, by weight of a compound of the present invention mixed with an edible organic or inorganic carrier, for example maize flour or maize and soya bean flour or mineral salts which preferably contain a small quantity of an edible antidust oil, for example, maize oil or soya bean oil. The resulting premix can then be added to the complete poultry feedstuff before feeding it to the animals.

The compounds of the present invention may also be mixed with animal drinking water for mass treatment or prophylaxis of coccidiosis.

The feedstuff may be used for both curative and prophylactic purposes.

For the treatment and prophylaxis of coccidiosis in poultry and particularly chickens, ducks, geese and turkeys, 25 to 100 ppm, preferably 50 to 100 ppm, of a compound according to the present invention is admixed with a suitable edible material, i.e. a nutritious feedstuff material. If desired, these amounts can be increased particularly where the compound is well tolerated by the recipient. The dosage can be lowered by combining the compound according to the present invention with imidazole-4,5-dicarboxylic acid amide or with a sulphonamide such as p-aminobenzenesulphonamides of 2-amino-4,6-dimethylpyrimidine, of 2-aminoquinoxaline, of 2-amino-5-methoxy-pyrimidine and of 2-amino-4-methyl-pyrimidine, because in such cases the combination results in an increase in overall activity level.

For the treatment of individual animals, for example in the case of treating coccidiosis in mammals or toxoplasmosis, it is preferred to administer amounts of 5 to 250 mg/kg of body weight per day in order to achieve the effective desired results. Nevertheless it can at times be necessary to deviate from the amounts mentioned and in particular to do so as a function of the body weight of the test animal or the nature of the method of administration but also because of the species of animal and its individual reaction to the medicine or the type of formulation and the time or interval at which it is administered. Thus, it can suffice in some cases to manage with less than the abovementioned minimum amount while in other cases the upper limit mentioned must be exceeded. Where major amounts are administered it can be advisable to divide these into several individual administrations over the course of the day.

The coccidiocidal activity of compounds representative of those of the present invention is illustrated in Tables 1 and 2 wherein *Eimeria tenella* (appendicecal coccidiosis/chickens) is shown as an example of the activity in the case of poultry coccidia, while *Eimeria falciformis* (mice) is shown as a coccidium in mammals.

TABLE 1

Comparison of the action of the componds of preparative Examples Nos.12 and 13 with that of 1-[(4-amino-2-propyl-5-pyrimidinyl)-methyl]-2-picolinium chloride hydrochloride (=A in the case of *Eimeria tenella*/chicks

| Criteria | Dose: 100 ppm in the feedstuff Preparative example | | | Dose: 50 ppm in the feedstuff Preparative example | | | Untreated infected control |
|---|---|---|---|---|---|---|---|
| | No.12 | No.13 | A | No.12 | No.13 | A | |
| Mortality rate | 0/6 | 0/6 | 0/5 | 0/6 | 0/6 | 0/5 | 2/6 |
| Oocyst excretion in % of the untreated infected control | 0% | 0% | 39% | 0.05% | 3% | 46% | 100% |
| Weight increase in % of the non-infected untreated control | 92% | 98% | 94% | 82% | 97% | 63% | 38% |
| Excretion of blood with the faeces x) | 0 | 0 | 0 | 0 | 0 | + | +++ |
| Macroscopic findings on dissection x) | 0 | 0 | ++ | 0 | 0 | ++ | +++ | x) The pathological changes and degree of excretion of blood, attributable to the infection, are coded as follows:
+++ = strong
++ = moderate
+ = slight
0 = no changes

TABLE 2

Comparison of the action o the componds of preparative Examples Nos. 11, 4, 12, 57 and 111 with that of 1-[(4-amino-2-propyl-5-pyrimidinyl)-methyl]-2-picolinium chloride hydrochloride (=A) in the case of a coccidium in mammals (*Eimeria falciformis*)

| Preparative example No. | Dose in mg/kg of body weight | | | | | | | | | |
|---|---|---|---|---|---|---|---|---|---|---|
| | 500 | 250 | 100 | 50 | 25 | 10 | 5 | 2.5 | 1 | 0.5 |
| 11 | 2 | 2 | 2 | 2 | 2 | 2 | 1 | 1 | 0 | |
| 4 | 2 | 2 | 2 | 2 | 2 | 1 | 1 | 0 | | |
| 12 | 2 | 2 | 2 | 2 | 1 | 0 | | | | |
| 57 | 2 | 2 | 2 | 2 | 2 | 2 | 2 | 1 | 1 | 0 |
| 111 | 2 | 2 | 2 | 1 | 0 | | | | | |
| A | 1 | 0 | | | | | | | | |

Legend:
2 = action
1 = slight action
0 = no action

If, for example, 11 day old chicks are infected with 30,000 sporulated oocysts of *Eimeria tenella*, the pathogen of appendiceal coccidiosis, 30 to 70% of the untreated controls die. The surviving chicks excrete daily 300,000 to 500,000 oocysts per gram (OpG) of faeces from the 7th to the 9th day after infection. In the course of the illness, the weight increase is substantially reduced and severe macroscopically detectable pathological changes occur in the appendices, which lead to severe haemorrhages. When testing the activity against *E. tenella* the compounds according to the invention were administered with the feedstuff from 3 days before infection to 9 days after infection (end of experiment).

The number of oocysts was determined by means of the McMaster chamber (see Engelbrecht et al., "Parasitologische Arbeitsmethoden in Medizin und Veterinarmedizin" (Parasitological Techniques in Medicine and Veterinary Medicine), page 172, Akademie-Verlag Berlin (1965)).

The treatment of the *Eimeria falciformis* infection in mice, which has been mentioned as an example of coccidia in mammals, took place on the 1st, 2nd, 3rd, 6th, 7th and 8th day after infection. The infection was carried out with 10,000 sporulated oocysts per mouse (weighing 15 g). In the case of the untreated controls, massive excretion of oocysts, diarrhoea containing blood and 30% mortality of the animals, attributable to the infection, occurred from the 7th day after infection onwards.

The following non-limitative examples more particularly illustrate the present invention:

EXAMPLE 1

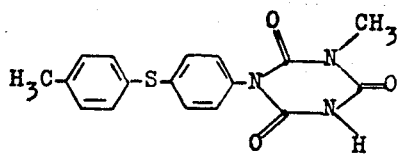

27.2 g (0.1 mol) of N-[4-(4'-methyl-phenylthio)-phenyl]-N'-methyl-urea were suspended in 300 ml of absolute toluene and 10.5 g (0.1 mol) of chlorocarbonylisocyanate were added dropwise at room temperature, while stirring. Thereafter, the mixture was stirred for a further hour at room temperature and 2 hours at the boil and after cooling the 1-[4-(4'-methyl-phenylthio)-phenyl]-3-methyl-1,3,5-triazine-2,4,6(1H,3H,5H)-trione which had separated out was filtered off and purified by stirring with alcohol or recrystallization therefrom; melting point 200°C, yield 87% of theory.

The following compounds were obtained in a manner analogous to that described above in Example 1:

Example No.

2  1-[4-(4'-tert.-butyl-phenylthio)-phenyl]-3-methyl-1,3,5-triazine-2,4,6(1H,3H,5H)-trione, melting point 212°C 3.  1-[4-(4'-acetamido-phenylthio)-phenyl]-3-methyl-1,3,5-triazine-2,4,6(1H,3H,5H)-trione, melting point 176°C 4  1-[4-(4'-ethoxycarbonylamino-phenylthio)-phenyl]-3-methyl-1,3,5-triazine-2,4,6(1H,3H,5H)-trione, melting point 231°C, from N-[4-(4'-ethoxycarbonylamino-phenylthio)-phenyl]-N'-methyl-urea, meltig poit 175°C and chlorocarbonylisocyanate.

5  1-[4-(4'-chloro-phenylthio)-3,5-dimethyl-phenyl]-3-methyl-1,3,5-triazine-2,4,6(1H,3H,5H)-trione, melting point 195°C 6  1-[3,5-dichloro-4-(4'-chloro-phenylthio)-phenyl]-3-methyl-1,3,5-triazine-2,4,6(1H,3H,5H)-trione, melting point 194°C 7  1-[4-(2',6'-dimethyl-4'-nitro-phenylthio)-phenyl]-3-methyl-1,3,5-triazine-2,4,6(1H,3H,5H)-trione, melting point 285°C 8  1-[4-(2',6'-dimethyl-4'-nitro-phenylthio)-phenyl]-3-propyl-1,3,5-triazine-2,4,6(1H,3H,5H)-trione, melting point 234°C 9  1-[2,5-dimethyl-4-(4'-methyl-phenylthio)-phenyl]-3-methyl-1,3,5-triazine-2,4,6(1H,3H,5H)-trione, melting point 193°C 10  1-[4-(4'-tert.-butyl-phenylthio)-2,5-dimethyl-phenyl]-3-methyl-1,3,5-triazine-2,4,6(1H,3H,5H)-trione, melting point 165°C 11  1-[4-(4'-nitro-phenylthio)-phenyl]-3-methyl-1,3,5-triazine-2,4,6(1H,3H,5H)-trione, melting point 194°C, from N-[4-(4'-nitro-phenylthio)-phenyl]-N'methyl-urea, melting point 220°C and chlorocarbonylisocyanate.

12  1-[4-(4'-nitro-phenylthio)-phenyl]-3-ethyl-1,3,5-triazine-2,4,6(1H,3H,5H)-trione, melting point 210°C, from N-[4-(4'-nitro-phenylthio)-phenyl]-N'-ethyl-urea, melting point 202°C and chlorocarbonylisocyanate 13  1-[4-(4'-nitro-phenylthio-phenyl] -3-propyl-1,3,5-triazine-2,4,6(1H,3H,5H)-trione, melting point 226°C, from N-[4-(4'-nitro-phenylthio)-phenyl]-N'-propyl-urea, melting point 195°C and chlorocarbonylisocyanate 14  1-[4-(4'-nitro-phenylthio)-phenyl]-3-butyl-1,3,5-triazine-2,4,6(1H,3H,5H)-trione, melting point 195°C, 15  1-[3,5-dichloro-4-(2',4',5'-trimethyl-phenylthio)-phenyl]-3-methyl-1,3,5-triazine-2,4,6(1H,3H,5H)-trione, melting point 231°C 16  1-[3,5-dichloro-4-(2',4'-dichloro-5'-methyl-phenylthio)-phenyl]-3-methyl-1,3,5,-triazine-2,4,6(1H,3H,5H)-trione, melting poit 234°C 17  1-[4-(3'-ethoxy-phenylthio)-3,5-dichloro-phenyl]-3-methyl-1,3,5-triazine-2,4,6(1H,3H,5H)-trione, melting point 178°C 18  1-[4-4'bromo-phenylthio)-3,5-dichloro-phenyl]-3-methyl-1,3,5-triazine-2,4,6(1H,3H,5H)-trione, melting poing 214°C 19  1-[4-(4'-bromo-phenylthio)-3,5-dimethyl-phenyl]-3-methyl-1,3,5-triazine-2,4,6(1H,3H,5H)-trione, melting point 199°C

| Example No. | |
|---|---|
| 20 | 1-[4-(4'-tert.-butyl-phenylthio)-3,5-dichloro-phenyl]-3-methyl-1,3,5-triazine-2,4,6(1H,3H,5H)-trione, melting point 192°C |
| 21 | 1-[4-(5'-chloro-2'-methyl-phenylthio)-3,5-dimethyl-phenyl]-3-methyl-1,3,5-triazine-2,4,6(1H,3H,5H)-trione, melting point 204°C |
| 22 | 1-[4-(2',5'-dimethoxy-phenylthio)-3,5-dimethyl-phenyl]-3-methyl-1,3,5-triazine-2,4,6(1H,3H,5H)-trione, melting point 113°C |
| 23 | 1-[4-(4'-chloro-phenylthio)-3,5-dimethyl-phenyl]-3-propyl-1,3,5-triazine-2,4,6(1H,3H,5H)-trione, melting point 79°C |
| 24 | 1-[3,5-dichloro-4-(4'-chloro-phenylthio)-phenyl]-3-propyl-1,3,5-triazine-2,4,6(1H,3H,5H)-trione, melting point 84°C |
| 25 | 1-[3,5-dichloro-4-(2',4',5'-trichloro-phenylthio)-phenyl]-3-methyl-1,3,5-triazine-2,4,6(1H,3H,5H)-trione, melting point 250°C |
| 26 | 1-[3,5-dichloro-4-(5'-chloro-2'-methyl-phenylthio)-phenyl]-3-methyl-1,3,5-triazine-2,4,6(1H,3H,5H)-trione, melting point 213°C |
| 27 | 1-[3,5-dichloro-4-(5'-chloro-2'-methoxy-phenylthio)-phenyl]-3-methyl-1,3,5-triazine-2,4,6(1H,3H,5H)-trione, melting point 138°C |
| 28 | 1-[3,5-dichloro-4-(2',5'-dimethoxy-phenylthio)-phenyl]-3-methyl-1,3,5-triazine-2,4,6(1H,3H,5H)-trione, melting point 132°C |
| 29 | 1-[3,5-dichloro-4-(4'-nitro-phenylthio)-phenyl]-3-methyl-1,3,5-triazine-2,4,6(1H,3H,5H)-trione, melting point 286°C |
| 30 | 1-[4-(2'-ethyl-phenylthio)-3,5-dichloro-phenyl]-3-methyl-1,3,5-triazine-2,4,6(1H,3H,5H)-trione, melting point 183°C |
| 31 | 1-[3,5-dichloro-4-(2',4'-dichloro-phenylthio)-phenyl]-3-propyl-1,3,5-triazine-2,4,6(1H,3H,5H)-trione, melting point 172°C |
| 32 | 1-[4-(2',6'-dimethoxy-phenylthio)-phenyl]-3-methyl-1,3,5-triazine-2,4,6(1H,3H,5H)-trione, melting point 275°C |
| 33 | 1-[3,5-dichloro-4-(4'-chloro-2'-methyl-phenylthio)-phenyl]-3-methyl-1,3,5-triazine-2,4,6(1H,3H,5H)-trione, melting point 101°C |
| 34 | 1-[3,5-dichloro-4-(2'-chloro-5'-trifluoromethyl-phenyl thio)-phenyl]-3-methyl-1,3,5-triazine-2,4,6(1H,3H,5H)-trione, melting point 194°C |
| 35 | 1-[3,5-dichloro-4-(2',4'-dichloro-phenylthio)-phenyl]-3-methyl-1,3,5-triazine-2,4,6(1H,3H,5H)-trione, melting point 104°C |
| 36 | 1-[3,5-dichloro-4-(2'-methoxy-5'-methyl-phenylthio)-phenyl]-3-methyl-1,3,5-triazine-2,4,6(1H,3H,5H)-trione, melting point 114°C |
| 37 | 1-[3,5-dichloro-4-(4'-chloro-2'-methoxy-phenylthio)-phenyl]-3-methyl-1,3,5-triazine-2,4,6(1H,3H,5H)-trione, melting point 124°C |
| 38 | 1-[3,5-dichloro-4-(4'-nitro-phenylthio)-phenyl]-3-propyl-1,3,5-triazine-2,4,6(1H,3H,5H)-trione, melting poing 173°C |
| 39 | 1-[4-(2'-chloro-4'-nitro-phenylthio)-phenyl]-3-methyl-1,3,5-triazine-2,4,6(1H,3H,5H)-trione, melting point 246°C |
| 40 | 1-[3,5-dichloro-4-(4'-nitro-phenylthio)-phenyl]-3-ethyl-1,3,5-triazine-2,4,6(1H,3H,5H)-trione, melting point 231°C |
| 41 | 1-[4-(2'-chloro-4'-cyano-phenylthio)-phenyl]-3-methyl-1,3,5-triazine-2,4,6(1H,3H,5H)-trione, melting point 278°C |
| 42 | 1-[4-(2'-chloro-4'-cyano-phenylthio)-phenyl]-3-ethyl-1,3,5-triazine-2,4,6(1H,3H,5H)-trione, melting point 245°C |
| 43 | 1-[3-chloro-4-(2',6'-dichloro-4'-nitro-phenylthio)-phenyl]-3-methyl-1,3,5-triazine-2,4,6(1H,3H,,5H)-trione, melting point 253°C |
| 44 | 1-[3,5-dichloro-4-(4'-nitro-phenylthio)-phenyl]-3-isopropyl-1,3,5-triazine-2,4,6(1H,3H,5H)-trione, melting point 130°C |
| 45 | 1-[4-(2'-chloro-4'-cyano-phenylthio)-phenyl]-3-propyl-1,3,5-triazine-2,4,6(1H,3H,5H)-trione, melting point 237°C |
| 46 | 1-[3,5-dichloro-4-(4'-nitro-phenylthio)-phenyl]-3-allyl-1,3,5-triazine-2,4,6(1H,3H,5H)-trione, melting point 130°C |
| 47 | 1-[4-(1'-chloro-4'-nitro-phenylthio)-phenyl]-3-ethyl-1,3,5-triazine-2,4,6(1H,3H,5H)-trione, melting point 211°C |
| 48 | 1-[3-chloro-4-(2',6'-dichloro-4'-nitro-phenylthio)-phenyl]-3-propyl-1,3,5-triazine-2,4,6-(1H,3H,5H)-trione, melting point 280°C |
| 49 | 1-[3,5-dichloro-4-(2'-chloro-4'-nitro-phenylthio)-phenyl[-3-ethyl-1,3,5-triazine-2,4,6(1H,3H,5H)-trione, melting point 217°C |
| 50 | 1-[3,5-dichloro-4-(2'-chloro-4'-nitro-phenylthio)-phenyl]-3-propyl-1,3,5-triazine-2,4,6(1H,3H,5H)-trione, melting point 162°C |
| 51 | 1-[3,5-dichloro-4-(2'-chloro-4'-nitro-phenylthio)-phenyl]-3-isopropyl-1,3,5-triazine-2,4,6(1H,3H,5H)-trione, melting point 180°C |
| 52 | 1-[3,5-dichloro-4-(2'-chloro-4'-nitro-phenylthio)-phenyl]-3-allyl-1,3,5-triazine-2,4,6(1H,3H,5H)-trione, melting point 137°C |
| 53 | 1-[4-(2',6'-dichloro-4'-nitro-phenylthio)-]-3-methyl-1,3,5-triazine-2,4,6(1H,3H,5H)-trione, melting point 280°C |
| 54 | 1-[4-(4'-acetamido-phenylthio)-phenyl]-3-propyl-1,3,5-triazine-2,4,6(1H,3H,5H)-trione, melting point 150°C, |
| 55 | 1-[3,5-dichloro-4-(2'-chloro-4'-nitro-phenylthio)-phenyl]-3-methyl-1,3,5-triazine-2,4,6(1H,3H,5H)-trione, melting point 258°C |
| 56 | 1-[4-(2',6'-dichloro-4'-nitro-phenylthio-phenyl]-3-ethyl-1,3,5-triazine-2,4,6(1H,3H,5H)-trione, melting point 266°C |
| 57 | 1-[4-(4'-cyano-phenylthio)-phenyl]-3-methyl-1,3,5-triazine-2,4,6(1H,3H,5H)-trione, melting point 207°C, from N-[4-(4'-cyano-phenylthio)-phenyl]-N'-methyl-urea, melting point 212°C, and chlorocarbonylisocyanate |
| 58 | 1-[4-(4'-cyano-phenylthio)-phenyl]-3-ethyl-1,3,5-triazine-2,4,6(1H,3H,5H)-trione, melting point 213°C, |
| 59 | 1-[3-chloro-4-(4'-nitro-phenylthio)-phenyl]-3-ethyl-1,3,5-triazine-2,4,6(1H,3H,5H)-trione, melting point 142°C |
| 60 | 1-[3-chloro-4-(4'-nitro-phenylthio)-phenyl]-3-methyl-1,3,5-triazine-2,4,6(1H,3H,5H)-trione, melting point 225°C |
| 61 | 1-[4-(4'-cyano-phenylthio)-phenyl]-3-propyl-1,3,5-triazine-2,4,6(1H,3H,5H)-trione, melting point 190°C, |
| 62 | 1-[3,5-dichloro-4-(2'-chloro-4'-cyano-phenylthio)-phenyl]-3-methyl-1,3,5-triazine-2,4,6(1H,3H,5H)-trione, melting point 278°C |
| 63 | 1-[4-(2'-chloro-4'-trifluoromethyl-phenylthio)-phenyl]-3-methyl-1,3,5-triazine-2,4,6(1H,3H,5H)-trione, melting point 148°C |
| 64 | 1-[4-(2'-chloro-4'-trifluoromethyl-phenylthio)-phenyl]-3-ethyl-1,3,5-triazine-2,4,6(1H,3H,5H)-trione, melting point 205°C |
| 65 | 1-[3-chloro-4-(4'-nitro-phenylthio)-phenyl]-3-propyl-1,3,5-triazine-2,4,6(1H,3H,5H)-trione, melting point 218°C |
| 66 | 1-[3,5-dichloro-4-(2'-chloro-4'-cyano-phenylthio)-phenyl]-3-ethyl-1,3,5-triazine-2,4,6(1H,3H,5H)-trione, melting point 267°C |
| 67 | 1-[4-(4'-trifluoromethyl-phenylthio)-phenyl]-3-propyl-1,3,5-triazine-2,4,6(1H,3H,5H)-trione, melting point 169°C |
| 68 | 1-[4-(4'-trifluoromethyl-phenylthio)-phenyl]-3-allyl-1,3,5-triazine-2,4,6(1H,3H,5H)-trione, melting point 168°C |
| 69 | 1-[3,5-dichloro-4-(2'-chloro-4'-trifluoromethyl-phenylthio)-phenyl]-3-methyl-1,3,5-triazine-2,4,6(1H,3H,5H)-trione, melting point 143°C |
| 70 | 1-[3,5-dichloro-4-(4'-trifluoromethyl-phenylthio)-phenyl]-3-propyl-1,3,5-triazine-2,4,6(1H,3H,5H)-trione, melting point 135°C |
| 71 | 1-[3,5-dichloro-4-(4'-cyano-phenylthio)-phenyl]-3-methyl-1,3,5-triazine-2,4,6(1H,3H,5H)-trione, melting point 148°C |
| 72 | 1-[3,5-dichloro-4-(4'-cyano-phenylthio)-phenyl]-3-propyl-1,3,5-triazine-2,4,6(1H,3H,5H)-trione, melting point 129°C |
| 73 | 1-[3,5-dichloro-4-(4'-cyano-phenylthio)-phenyl]-3-ethyl-1,3,5-triazine-2,4,6(1H,3H,5H)-trione, melting point 152°C |
| 74 | 1-[4-(4'-nitro-phenylthio)-phenyl]-3-isopropyl-1,3,5-triazine-2,4,6(1H,3H,5H)-trione, melting pont 180°C, |
| 75 | 1-[4-(4'-nitro-phenylthio)-phenyl]-3-allyl-1,3,5-triazine-2,4,6(1H,3H,5H)-trione, melting point 223°C, |
| 76 | 1-[4-(4'-nitro-phenylthio)-phenyl]-3-tert.-butyl-1,3,5-triazine-2,4,6(1H,3H,5H)-trione, melting point 183°C |
| 77 | 1-[4-(4'-nitro-phenylthio)-phenyl]-3-(2-methoxy-ethyl)-1,3,5-triazine-2,4,6(1H,3H,5H)-trione, melting point 241°C |
| 78 | 1-[4-(4'-nitro-phenylthio)-phenyl]-3-(3-ethoxy-propyl)-1,3,5-triazine-2,4,6(1H,3H,5H)-trione, melting point 138°C |
| 79 | 1-[4-(4'-nitro-phenylthio)-phenyl]-3-(3-methoxy-propyl)-1,3,5-triazine-2,4,6(1H,3H,5H)-trione, melting point 165°C |
| 80 | 1-[4-(4'-chloro-phenylthio)-phenyl]-3-methyl-1,3,5-triazine-2,4,6(1H,3H,5H)-trione, melting point 204°C, |
| 81 | 1-[4-(4'-chloro-phenylthio)-phenyl]-3-ethyl-1,3,5-triazine-2,4,6(1H,3H,5H)-trione, melting point 159°C, |
| 82 | 1-[4-(4'-chloro-phenylthio)-phenyl]-3-propyl-1,3,5-triazine-2,4,6(1H,3H,5H)-trione, melting point 202°C, |
| 83 | 1-[3-chloro-4-(4'-chloro-phenylthio)-5-methyl-phenyl]-3-ethyl-1,3,5-triazine-2,4,6(1H,3H,5H)-trione, melting point 189°C |
| 84 | 1-[3-chloro-4-(4'-chloro-phenylthio)-5-methyl-phenyl]- |

| Example No. | |
|---|---|
| | 3-butyl-1,3,5-triazine-2,4,6(1H,3H,5H)-trione, melting point 145°C |
| 85 | 1-[3-chloro-4-(4'-chloro-phenylthio)-5-methyl-phenyl]-3-allyl-1,3,5-triazine-2,4,6(1H,3H,5H)-trione, melting pont 130°C |
| 86 | 1-[4-(5'-chloro-2'-methoxy-phenylthio)-3,5-dimethyl-phenyl]-3-ethyl-1,3,5-triazine-2,4,6(1H,3H,5H)-trione, melting point 198°C |
| 87 | 1-[4-(4'-acetyl-phenylthio)-3,5-dimethyl-phenyl]-3-methyl-1,3,5-triazine-2,4,6(1H,3H,5H)-trione, melting point 234 – 235°C |
| 88 | 1-[4-(4'-acetyl-phenylthio)-3,5-dichloro-phenyl]-3-methyl-1,3,5-triazine-2,4,6(1H,3H,5H)-trione, melting point 225 – 226°C |
| 89 | 1-[4-(5'-chloro-2'-methyl-phenylthio)-3,5-dimethyl-phenyl]-3-ethyl-1,3,5-triazine-2,4,6(1H,3H,5H)-trione, melting point 190°C |
| 90 | 1-[3,5-dichloro-4-(2',5'-dimethoxy-phenylthio)-phenyl]-3-ethyl-1,3,5-triazine-2,4,6(1H,3H,5H)-trione, melting point 194°C |
| 91 | 1-[4-(2',5'-dimethoxy-phenylthio)-3,5-dimethyl-phenyl]-3-ethyl-1,3,5-triazine-2,4,6(1H,3H,5H)-trione, melting point 124 – 126°C |
| 92 | 1-[4-(2'-chloro-6'-methyl-4'-nitro-phenylthio)-phenyl]-3-ethyl-1,3,5-triazine-2,4,6(1H,3H,5H)-trione, melting point 261 – 263°C |
| 93 | 1-[3-chloro-4-(2',4'-dichloro-phenylthio)-phenyl]-3-methyl-1,3,5-triazine-2,4,6(1H,3H,5H)-trione, melting point 216°C |
| 94 | 1-[3-chloro-4-(2',4'-dichloro-phenylthio)-phenyl]-3-ethyl-1,3,5-triazine-2,4,6(1H,3H,5H)-trione, melting point 160°C |
| 95 | 1-[4-(4'-methyl-phenylthio)-phenyl]-3-ethyl-1,3,5-triazine-2,4,6(1H,3H,5H)-trione, melting point 220°C, |
| 96 | 1-[4-(4'-nitro-phenylthio)-phenyl]-1,3,5-triazine-2,4,6(1H,3H,5H)-trione, melting point 261°C |
| 97 | 1-[4-(4'-methylsulphonyl-phenylthio)-phenyl]-3-methyl-1,3,5-triazine-2,4,6(1H,3H,5H)-trione, melting point 160°C |
| 98 | 1-[4-(4'-trifluoromethyl-phenylthio)-phenyl]-3-ethyl-1,3,5-triazine-2,4,6(1H,3H,5H)-trione, melting point 194°C |
| 99 | 1-[3,5-dichloro-4-(4'-trifluoromethyl-phenylthio)-phenyl]-3-methyl-1,3,5-triazine-2,4,6(1H,3H,5H)-trione, melting point 195 – 196°C |
| 100 | 1-[4(4'-nitro-phenylthio)-phenyl]-3-methyl-1,3,5-triazine-2-thioxo-4,6(1H,3H,5H)-dione, melting point 260°C |
| 101 | 1-[4-(4'-nitro-phenylthio)-phenyl]-3-ethyl-1,3,5-triazine-2-thioxo-4,6(1H,3H,5H)-dione, melting point 224°C |
| 102 | 1-[4-(2'-chloro-6'-methyl-4'-nitro-phenylthio)-phenyl]-3-methyl-1,3,5-triazine-2,4,6(1H,3H,5H)-trione, melting point 285 – 286°C |
| 103 | 1-[4-(2'-chloro-6'-methyl-4'-nitro-phenylthio)-phenyl]-3-propyl-1,3,5-triazine-2,4,6(1H,3H,5H)-trione, melting point 242 – 244°C |
| 104 | 1-[4-(4'-nitro-phenylthio)-phenyl]-3-phthalimido-1,3,5-triazine-2,4,6(1H,3H,5H)-trione, melting point 284 – 285°C |
| 104a | 1-[3,5-dichloro-4-(2'-chloro-6'-methyl-4'-nitro-phenylthio)-phenyl]-3-methyl-1,3,5-triazine-2,4,6 (1H,3H,5H)-trione, melting point 280°C |
| 104b | 1-[3,5-dichloro-4-(2'-chloro-6'-methyl-4'-nitro-phenylthio)-phenyl]-3-propyl-1,3,5-triazine-2,4,6 (1H,3H,5H)-trione, melting point 231°C |
| 104c | 1-[4-(4'-ethoxycarbonylamino-phenylthio)-phenyl]-3-ethyl-1,3,5-triazine-2,4,6(1H,3H,5H)-trione, melting point 212°C |
| 104d | 1-[4-(4'-ethoxycarbonylamino-phenylthio)-phenyl]-3-butyl-1,3,5-triazine-2,4,6(1H,3H,5H)-trione, melting point 132°C |
| 104e | 1-[4-(4'-chloro-phenylthio)-phenyl]-3-butyl-1,3,5-triazine-2,4,6(1H,3H,5H)-trione, melting point 192°C, |
| 104f | 1-[4-(4'-chloro-phenylthio)-phenyl]-3-allyl-1,3,5-triazine-2,4,6(1H,3H,5H)-trione, melting point 171°C |
| 104g | 1-[4-(4'-trifluoromethoxy-phenylthio)-phenyl]-3-ethyl-1,3,5-triazine-2,4,6(1H,3H,5H)-trione, melting point 240°C |
| 104h | 1-[4-(4'-nitro-phenylthio)-phenyl]-3-ethoxy-1,3,5-triazine-2,4,6(1H,3H,5H)-trione, melting point 216°C, |
| 104i | 1-[4-(4'-nitro-phenylthio)-phenyl]-3-methoxy-1,3,5-triazine-2,4,6(1H,3H,5H)-trione, melting point 202°C, |
| 104k | 1-[4-(4'-methylsulphonyl-phenylthio)-phenyl]-3-ethyl-1,3,5-triazine-2,4,6(1H,3H,5H)-trione, melting point 178°C |
| 104L | 1-[4-(3'-cyano-4'-4'-nitro-phenylthio)-phenyl]-3-propyl-1,3,5-triazine-2,4,6(1H,3H,5HO-trione, melting point 205°C |

EXAMPLE 105

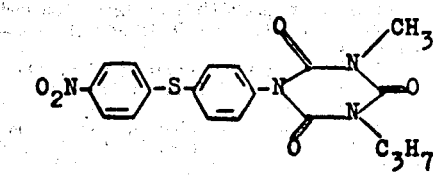

The dry residue from the reaction of an 0.1 molar sodium ethylate solution with 40 g (0.1 mol) of 1-[4-(4'-nitro-phenylthio)-phenyl]-3-propyl-1,3,5-triazine-2,4,6 (1H,3H,5H)-trione, of melting point 226°C, is dissolved in 250 ml of dimethylformamide and 14.2 g (0.1 mol) of methyl iodide — diluted with a few ml of DMF — are added dropwise at room temperature, while stirring. The mixture is then warmed for 2 hours at 50°C, the solvent is then stripped off in vacuo, the residue is thoroughly stirred with water, and after drying the 1-[4-(4'-nitrophenylthio)-phenyl]-3-methyl-5-propyl-1,3,5-triazine-2,4,6(1H,3H,5H)-trione is recrystallized from chlorobenzene/ligroin; melting point 187°C, yield 56% of theory.

EXAMPLE 106

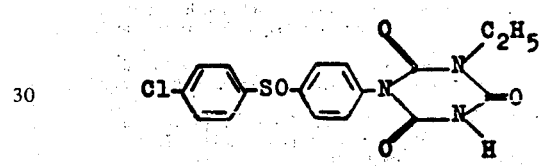

8.5 g (0.023 mol) of 1-[4-(4'-chloro-phenylthio)-phenyl]-3-ethyl-1,3,5-triazine-2,4,6(1H,3H,5H)-trione, 2.5 ml of 30 per cent strength hydrogen peroxide and 45 ml of acetic anhydride are stirred for 16 hours at 35° – 40°C (bath temperature). After cooling, the precipitate is filtered off, suspended in aqueous sodium bicarbonate solution, again filtered off, washed with water and dried, 5.2 g (58% of theory) of 1-[4-(4'-chloro-phenyl-sulphinyl)-phenyl]-3-ethyl-1,3,5-triazine-2,4,6(1H,3H,5H)-trione, of melting point 275° – 277°C, are obtained from dioxane/water.

The following compound is obtained in a manner analogous to that described above in Example 106:

EXAMPLE 107

1-[4-(4'-nitro-phenylsulphinyl)-phenyl]-3-propyl-1,3,5-triazine-2,4,6(1H,3H,5H)-trione, melting point 255°C

EXAMPLE 108

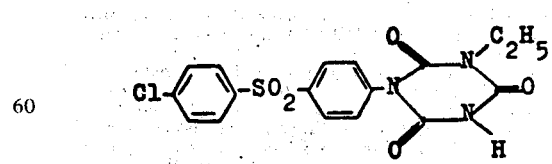

9.35 g (0.025 mol) of 1-[4-(4'-chloro-phenylthio)-phenyl]-3-ethyl-1,3,5-triazine-2,4,6(1H,3H,5H)- trione, 40 ml of 30 per cent strength hydrogen peroxide and 40 ml of glacial acetic acid are heated to the boil for 16 hours, while stirring. After cooling, a little water is added and the precipitate is filtered off, suspended in aqueous sodium bicarbonate solution, again filtered off, washed with water and dried. 8.2 g (80% of theory) of 1-[4-(4'-chloro-phenylsulphonyl)-phenyl]-3-ethyl-1,3,5-triazine-2,4,6(1H,3H,5H)-trione, of melting point 315° – 317°C, are obtained from acetonitrile.

The following compounds were obtained in a manner analogous to that described above in Example 108:

| Example No. | |
|---|---|
| 109 | 1-(4-phenylsulphonyl-phenyl)-3-methyl-1,3,5-triazine-2,4,6(1H,3H,5H)-trione, melting point 278°C |
| 110 | 1-[4-(4'-nitro-phenylsulphonyl)-phenyl]-3-methyl-1,3,5-triazine-2,4,6(1H,3H,5H)-trione, melting point 277°C |
| 111 | 1-[4-(4'-chloro-phenylsulphonyl)-phenyl]-3-methyl-1,3,5-triazine-2,4,6(1H,3H,5H)-trione, melting point 251°C, from N-[4-(4'-chloro-phenylsulphonyl)-phenyl]-N'-methyl-urea, melting point 193°C, and chlorocarbonyl isocyanate |
| 112 | 1-[4-(4'-nitro-phenylsulphonyl)-phenyl]-3-propyl-1,3,5-triazine-2,4,6(1H,3H,5H)-trione, melting point 279°C |
| 113 | 1-[4-(4'-nitro-phenylsulphonyl)-phenyl]-3-ethyl-1,3,5-triazine-2,4,6(1H,3H,5H-trione, melting point 296°C |
| 114 | 1-[4-(4'-nitro-phenylsulphonyl)-phenyl]-3-allyl-1,3,5-triazine-2,4,6(1H,3H,5H)-trione, melting point 267°C |
| 115 | 1-[4-(4'-nitro-phenylsulphonyl)-phenyl]-3-isopropyl-1,3,5-triazine-2,4,6(1H,3H,5H)-trione, melting point 272°C, from |
| 116 | 1-[3,5-dichloro-4-(5'-chloro-2'-methoxy-phenylsulphonyl)-phenyl]-3-methyl-1,3,5-triazine-2,4,6)1H,3H,5H)-trione, melting point 267°C |
| 117 | 1-(4-(4'-chloro-phenylsulphonyl)-phenyl]-3-propyl-1,3,5-triazine-2,4,6(1H,3H,5H)-trione, melting point 221°C |
| 118 | 1-[4-(5'-chloro-2'-methoxy-phenylsulphonyl)-3,5-dimethyl-phenyl]-3-ethyl-1,3,5-triazine-2,4,6(1H,3H,5H)-trione, melting point 159°C |
| 119 | 1-[3,5-dichloro-4-(2'-methoxy-5'-methyl-phenylsulphonyl)-phenyl]-3-methyl-1,3,5-triazine-2,4,6(1H,3H,5H)-trione, melting point 199°C |
| 120 | 1-[4-(2'-chloro-6'-methyl-4'-nitro-phenylsulphonyl)-phenyl]-3-ethyl-1,3,5-triazine-2,4,6(1H,3H,5H)-trione, melting point 255 – 256°C |
| 121 | 1-[4-(2'-chloro-6'-methyl-4'-nitro-phenylsulphonyl)-phenyl]-3-n-propyl-1,3,5-triazine-2,4,6(1H,3H,5H)-trione, melting point 242 – 243°C |
| 122 | 1-[4-(4'-methylsulphonyl-phenylsulphonyl)-phenyl]-3-ethyl-1,3,5-triazine-2,4,6(1H,3H,5H)-trione, melting point 265°C |
| 123 | 1-[4-(4'-methyl-phenylsulphonyl)-phenyl]-3-ethyl-1,3,5-triazine-2,4,6(1H,3H,5H)-trione, melting point 341°C |
| 124 | 1-[4-(4'-trifluoromethyl-phenylsulphonyl)-phenyl]-3-ethyl-1,3,5-triazine-2,4,6(1H,3H,5H)-trione, melting point 273°C |
| 125 | 1-[3,5-dichloro-4-(4'-trifluoromethyl-phenylsulphonyl)-phenyl]-3-methyl-1,3,5-triazine-2,4,6(1H,3H,5H)-trione, melting point 243 – 244°C |
| 125a | 1-[4-(2'-chloro-6'-methyl-4'-nitro-phenylsulphonyl)-phenyl]-3-methyl-1,3,5-triazine-2,4,6(1H,3H,5H)-trione, melting point 265°C |
| 125b | 1-[4-(4'-chloro-phenylsulphonyl)-phenyl]-3-allyl-1,3,5-triazine-2,4,6(1H,3H,5H)-trione, melting point 270°C |
| 125c | 1-[4(4'-chloro-phenylsulphonyl)-phenyl]-3-butyl-1,3,5-triazine-2,4,6(1H,3H,5H)-trione, melting poin 209°C |

The following example illustrates the production of starting materials used to produce the compounds of the present invention:

EXAMPLE A

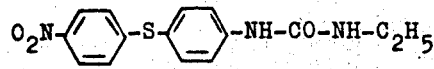

74 g (0.3 mol) of 4-amino-4'-nitro-diphenyl sulphide of melting point 144°C, 300 ml of dry pyridine and 21.3 g (0.3 mol) of ethylisocyanate were warmed to 90°C for 8 hours, while stirring. After cooling, the N-[4-(4'-nitrophenylthio)-phenyl]-N'-ethyl-urea which has crystallized out is filtered off and further purified by recrystallization from chlorobenzene. Melting point 203°C, yield 60 g 63% of theory; the yield can be increased by working up the mother liquor.

The following ureas were obtained in a manner analogous to that described above in Example A N-[4-(4'-methyl-phenylthio)-phenyl]-N'-methyl-urea, melting point 166°C N-[4-(4'-tert.-butyl-phenylthio)-phenyl]-N'-methyl-urea, melting point 175°C N-[4-(4'-acetamido-phenylthio)-phenyl]-N'-methyl-urea, melting point 190°C N-[4-(4'-ethoxycarbonylamino-phenylthio)-phenyl]-N'-methyl-urea, melting point 175°C N-[4'(4'-chloro-phenylthio)-3,5-dimethyl-phenyl]-N'-methyl-urea, melting point 193°C N-[3,5-dichloro-4-(4'-chloro-phenylthio)-phenyl]-N'-methyl-urea, melting point 204°C N-[4-(2',6'-dimethyl-4'-nitro-phenylthio)-phenyl]-N'-methyl-urea, melting point 214°C N-[4-(2',6'-dimethyl-4'-nitro-phenylthio)-phenyl]-N'-propyl-urea, melting point 215°C N-[2,5-dimethyl-4-(4'-methyl-phenylthio)-phenyl]-N'-methyl-urea, melting point 218°C N-[4-(4'-tert.-butyl-phenylthio)-2,5-dimethyl-phenyl]-N'-methyl-urea, melting point 197°C N-[4-(4'-nitro-phenylthio)-phenyl]-N'-methyl-urea, melting point 220°C N-[4-(4'-nitro-phenylthio)-phenyl]-N'-propyl-urea, melting point 195°C N-[4-(4'-nitro-phenylthio)-phenyl]-N'-butyl-urea, melting point 188°C N-[3,5-dichloro-4-(2',4',5'-trimethyl-phenylthio)-phenyl]-N'-methyl-urea, melting point 111°C N-[3,5-dichloro-4-(2',4'-dichloro-5'-methyl-phenylthio)-phenyl]-N'-methyl-urea, melting point 250°C N-[4-(3'-ethoxy-phenylthio)-3,5-dichloro-phenyl]-N'-methyl-urea, melting point 165°C N-[4-(4'-bromo-phenylthio)-3,5-dichloro-phenyl]-N'-methyl-urea, melting point 203°C N-[4-(4'-bromo-phenylthio)-3,5-dimethyl-phenyl]-N'-methyl-urea, melting point 199°C N-[4-(4'-tert.-butyl-phenylthio)-3,5-dichloro-phenyl]-N'-methyl-urea, melting point 244°C N-[4-(5'-chloro-2'-methyl-phenylthio)-3,5-dimethyl-phenyl]-N'-methyl-urea, melting point 225°C N-[4-(2',5'-dimethoxy-phenylthio)-3,5-dimethyl-phenyl]-N'-methyl-urea, melting point 169°C N-[4-(4'-chloro-phenylthio)-3,5-dimethyl-phenyl]-N'-propyl-urea, melting point 142°C N-[3,5-dichloro-4-(4'-chloro-phenylthio)-phenyl]-N'-propyl-urea, melting point 153°C N-[3,5-dichloro-4-(2',4',5'-trichloro-phenylthio)-phenyl]-N'-methyl-urea, melting point 239°C N-[3,5-dichloro-4-(5'-chloro-2'-methyl-phenylthio)-phenyl]-N'-methyl-urea, melting point 199°C N-[3,5-dichloro-4-(5'-chloro-2'-methoxy-phenylthio)-phenyl]-N'-methyl-urea, melting point 202°C N-[3,5-dichloro-4-(2',5'-dimethoxy-phenylthio)-phenyl]-N'-methyl-urea, melting point 153°C
N-[3,5-dichloro-4-(4'-nitro-phenylthio)-phenyl]-N'-methyl-urea, melting point 260°C
N-[4-(2'-ethyl-phenylthio)-3,5-dichloro-phenyl]-N'-methyl-urea, melting point 202°C
N-[3,5-dichloro-4-(2',4'-dichloro-phenylthio)-phenyl]-N'-propyl-urea, melting point 265°C
N-[4-(2',6'-dimethoxy-phenylthio)-phenyl]-N'-methyl-urea, melting point 210°C
N-[3,5-dichloro-4-(4'-chloro-2'-methyl-phenylthio)-phenyl]-N'-methyl-urea, melting point 205°C
N-[3,5-dichloro-4-(2'-chloro-5'-trifluoromethyl-phenylthio)-phenyl]-N'-methyl-urea, melting point 225°C,
N-[3,5-dichloro-4-(2',4'-dichloro-phenylthio)-phenyl]-N'-methyl-urea, melting point 221°C
N-[3,5-dichloro-4-(2'-methoxy-5'-methyl-phenylthio)-phenyl]-N'-methyl-urea, melting point 205°C
N-[3,5-dichloro-4-(4'-chloro-2'-methoxy-phenylthio)-phenyl]-N'-methyl-urea, melting point 178°C
N-[3,5-dichloro-4-(4'-nitro-phenylthio)-phenyl]-N'-propyl-urea, melting point 246°C
N-[4-(2'-chloro-4'-nitro-phenylthio)phenyl]-N'-methyl-urea, melting point 199°C
N-[3,5-dichloro-4-(4'-nitro-phenylthio)-phenyl]-N'-ethyl-urea, melting point 270°C
N-[4-(2'-chloro-4'-cyano-phenylthio)-phenyl]-N'-methyl-urea, melting point 189°C
N-[4-(2'-chloro-4'-cyano-phenylthio)-phenyl]-N'-ethyl-urea, melting point 180°C
N-[3-chloro-4-(2',6'-dichloro-4'-nitro-phenylthio)-phenyl]-N'-methyl-urea, melting point 232°C
N-[3,5-dichloro-4-(4'-nitro-phenylthio)-phenyl]-N'-isopropyl-urea, melting point 260°C
N-[4-(2'-chloro-4'-cyano-phenylthio)-phenyl]-N'-propyl-urea, melting point 186°C
N-[3,5-dichloro-4-(4'-nitro-phenylthio)-phenyl]-N'-allyl-urea, melting point 237°C
N-[4-(2'-chloro-4'-nitro-phenylthio)-phenyl]-N'-ethyl-urea, melting point 218°C
N-[3-chloro-4-(2',6'-dichloro-4'-nitro-phenylthio)-phenyl]-N'-propyl-urea, melting point 111°C
N-[3,5-dichloro-4-(2'-chloro-4'-nitro-phenylthio)-phenyl]-N'-ethyl-urea, melting point 249°C
N-[3,5-dichloro-4-(2'-chloro-4'-nitro-phenylthio)-phenyl]-N'-propyl-urea, melting point 235°C
N-[3,5-dichloro-4-(2'-chloro-4'-nitro-phenylthio)-phenyl]-N'-isopropyl-urea, melting point 217°C
N-[3,5-dichloro-4-(2'-chloro-4'-nitro-phenylthio)-phenyl]-N'-allyl-urea, melting point 227°C
N-[4-(2',6'-dichloro-4'-nitro-phenylthio)-phenyl]-N'-methyl-urea, melting point 229°C
N-[4-(4'-acetamido-phenylthio)-phenyl]-N'-propyl-urea, melting point 216°C
N-[3,5-dichloro-4-(2'-chloro-4'-nitro-phenylthio)-phenyl]-N'-methyl-urea, melting point 237°C
N-[4-(2',6'-dichloro-4'-nitro-phenylthio)-phenyl]-N'-ethyl-urea, melting point 225°C
N-[4-(4'-cyano-phenylthio)-phenyl]-N'-methyl-urea, melting point 212°C
N-[4-(4'-cyano-phenylthio)-phenyl]-N'-ethyl-urea, melting point 193°C
N-[3-chloro-4-(4'-nitro-phenylthio)-phenyl]-N'-ethyl-urea, melting point 156°C
N-[3-chloro-4-(4'-nitro-phenylthio)-phenyl]-N'-methyl-urea, melting point 163°C
N-[4-(4'-cyano-phenylthio)-phenyl]-N'-propyl-urea, melting point 183°C
N-[3,5-dichloro-4-(2'-chloro-4'-cyano-phenylthio)-phenyl]-N'-methyl-urea, melting point 235°C
N-[4-(2'-chloro-4'-trifluoromethyl-phenylthio)-phenyl]-N'-methyl-urea, melting point 194°C
N-[4-(2'-chloro-4'-trifluoromethyl-phenylthio)-phenyl]-N'-ethyl-urea, melting point 173°C
N-[3-chloro-4-(4'-nitro-phenylthio)-phenyl]-N'-propyl-urea, melting point 126°C
N-[3,5-dichloro-4-(2'-chloro-4'-cyano-phenylthio)-phenyl]-N'-ethyl-urea, melting point 248°C
N-[4-(4'-trifluoromethyl-phenylthio)-phenyl]-N'-propyl-urea, melting point 176°C
N-[4-(4'-trifluoromethyl-phenylthio)-phenyl]-N'-allyl-urea, melting point 164°C
N-[3,5-dichloro-4-(2'-chloro-4'-trifluoromethyl-phenylthio)-phenyl]-N'-methyl-urea, melting point 262°C
N-[3,5-dichloro-4-(4'-trifluoromethyl-phenylthio)-phenyl]-N'-propyl-urea, melting point 252°C
N-[3,5-dichloro-4-(4'-cyano-phenylthio)-phenyl]-N'-methyl-urea, melting point 219°C
N-[3,5-dichloro-4-(4'-cyano-phenylthio)-phenyl]-N'-propyl-urea, melting point 244°C
N-[3,5-dichloro-4-(4'-cyano-phenylthio)-phenyl]-N'-ethyl-urea, melting point 247°C
N-[4-(4'-chloro-phenylthio)-phenyl]-N'-methyl-urea, melting point 193°C
N-[4-(4'-chloro-phenylthio)-phenyl]-N'-ethyl-urea, melting point 172°C
N-[4-(4'-chloro-phenylthio)-phenyl]-N'-propyl-urea, melting point 178°C
N-[3-chloro-4-(4'-chloro-phenylthio)-5-methyl-phenyl]-N'-ethyl-urea, melting point 218°C
N-[3-chloro-4-(4'-chloro-phenylthio)-5-methyl-phenyl]-N'-butyl-urea, melting point 184°C
N-[3-chloro-4-(4'-chloro-phenylthio)-5-methyl-phenyl]-N'-allyl-urea, melting point 204°C
N-[4-(5'-chloro-2'-methoxy-phenylthio)-3,5-dimethyl-phenyl]-N'-ethyl-urea, melting point 182°C
N-[4-(4'-acetyl-phenylthio)-3,5-dimethyl-phenyl]-N'-methyl-urea, melting point 160°C
N-[4-(4'-acetyl-phenylthio)-3,5-dichloro-phenyl]-N'-methyl-urea, melting point 220°C
N-[4-(5'-chloro-2'-methyl-phenylthio)-3,5-dimethyl-phenyl]-N'-ethyl-urea, melting point 230°C
N-[3,5-dichloro-4-(2',5'-dimethoxy-phenylthio)-phenyl]-N'-ethyl-urea, melting point 123°C
N-[4-(2',5'-dimethoxy-phenylthio)-3,5-dimethyl-phenyl]-N'-ethyl-urea, melting point 149°C
N-[4-(2'-chloro-6'-methyl-4'-nitro-phenylthio)-phenyl]-N'-ethyl-urea, melting point 213°C
N-[3,5-dichloro-4-(2'-chloro-6'-methyl-4'-nitro-phenylthio)-phenyl]-N'-ethyl-urea, melting point 242°C
N-[4-(2'-chloro-6'-methyl-4'-nitro-phenylthio)-phenyl]-N'-methyl-urea, melting point 212°C
N-[4-(2'-chloro-6'-methyl-4'-nitro-phenylthio)-phenyl]-N'-propyl-urea, melting point 184°C
N-[3-chloro-4-(2',4'-dichloro-phenylthio)-phenyl]-N'-methyl-urea, melting point 159°C
N-[3-chloro-4-(2',4'-dichloro-phenylthio)-phenyl]-N'-ethyl-urea, melting point 185°C
N-[4-(4'-methyl-phenylthio)-phenyl]-N'-ethyl-urea, melting point 121°C
N-[4-(4'-methyl-sulphonyl-phenylthio)-phenyl]-N'-ethyl-urea, melting point 195°C N-[4-(4'-trifluoromethyl-phenylthio)-phenyl]-N'-ethyl-urea, melting point 210°C
N-[3,5-dichloro-4-(4'-trifluoromethyl-phenylthio)-phenyl]-N'-methyl-urea, melting point 247°C
N-[4-(4'-nitro-phenylthio)-phenyl]-N'-isopropyl-urea, melting point 225°C
N-[4-(4'-nitro-phenylthio)-phenyl]-N'-allyl-urea, melting pont 187°C
N-[4-(4'-nitro-phenylthio)-phenyl-N'-tert.-butyl-urea, melting point 224°C
N-[4-(4'-nitro-phenylthio)-phenyl]-N'-(methoxymethyl)-urea, melting point 203°C
N-[4-(4'-nitro-phenylthio)-phenyl]-N'-(2-methoxyethyl)-urea, melting point 152°C
N-[4-(4'-nitro-phenylthio)-phenyl]-N'-(3-methoxypropyl)-urea, melting point 146°C
N-[4-(4'-nitro-phenylthio)-phenyl]-N'-(3-ethoxypropyl)-urea, melting point 148°C
N-[4-(4'-nitro-phenylthio)-phenyl]-N'-phthalimido-urea, melting point 231°C
N-[4-(4'-nitro-phenylthio)-phenyl]-urea, melting point 211°C
N-[4-phenylsulphonyl-phenyl]-N'-methyl-urea, melting point 181°C
N-[4-(4'-nitro-phenylsulphonyl)-phenyl]-N'-methyl-urea, melting point 224°C
N-[4-(4'-chloro-phenylsulphonyl)-phenyl]-N'-methyl-urea, melting point 193°C
N-[4-(4'-nitro-phenylsulphonyl)-phenyl]-N'-propyl-urea, melting point 156°C
N-[4-(4'-nitro-phenylsulphonyl)-phenyl]-N'-ethyl-urea, melting point 193°C
N-[4-(4'-nitro-phenylsulphonyl)-phenyl]-N'-allyl-urea, melting point 158°C
N-[4-(4'-nitro-phenylsulphonyl)-phenyl]-N'-isopropyl-urea, melting point 129°C
N-[4-(4'-chloro-phenylsulphonyl)-phenyl]-N'-ethyl-urea, melting point 184°C
N-[4-(4'-chloro-phenylsulphonyl)-phenyl]-N'-propyl-urea, melting point 178°C
N-[4-(4'-methyl-phenylsulphonyl)-phenyl]-N'-ethyl-urea, melting point 218°C
N-[4-(4'-trifluoromethyl-phenylsulphonyl)-phenyl]-N'-ethyl-urea, melting point 182°C
N-[4-(4'-nitro-phenylthio)-phenyl]-N'-methyl-thiourea, melting point 191°C
N-[4-(4'-nitro-phenylthio)-phenyl]-N'-ethyl-thiourea, melting point 160°C

What is claimed is:
1. A pharmaceutical composition useful for the treatment of and prophylaxis against coccidiosis in humans and animals which comprises a therapeutically effective amount of a compound of the formula:

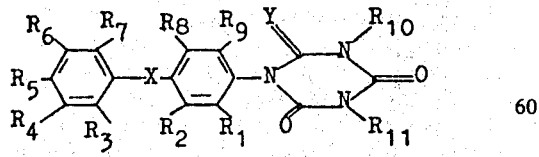

or a pharmaceutically acceptable nontoxic salt thereof wherein
$R_1$, $R_2$, $R_3$, $R_4$, $R_5$, $R_6$, $R_7$, $R_8$ and $R_9$ are the same or different and each is selected from the group consisting of hydrogen, straight or branched chain lower alkyl, halo lower alkyl, lower alkoxy, halo lower alkoxy, lower alkylthio, halo lower alkylthio, halogen, nitro, cyano, amino, lower alkanoylamino, lower alkoxycarbonylamino, carboxy, lower alkoxycarbonyl, carbamoyl, lower alkanoyl, halo lower alkanoyl, lower alkylsulphinyl, lower alkylsulphonyl, halo lower alkylsulphonyl, and sulphamoyl;

$R_{10}$ is hydrogen, straight or branched chain lower alkyl, cycloalkyl of 3 to 7 carbon atoms, halo lower alkyl, lower alkoxy, lower alkoxy lower alkyl, halo lower alkoxy lower alkyl, lower alkylthio lower alkyl, halo lower alkylthio lower alkyl, lower alkenyl, lower alkynyl, lower alkoxycarbonyl, (lower alkylthio)carbonyl, (lower alkylthio)thiocarbonyl, lower alkanoylamino, succinimido, phthalimido, amino, dilower alkylamino, benzyl, phenyl, or benzyl or phenyl substituted by halogen;

$R_{11}$ is hydrogen or lower alkyl;
X is sulphur, sulphinyl or sulphonyl; and
Y is oxygen or sulphur; in combination with a pharmaceutically acceptable nontoxic inert diluent or carrier.

2. A composition according to claim 1 wherein
$R_1$, $R_2$, $R_3$, $R_4$, $R_5$, $R_6$, $R_7$, $R_8$ and $R_9$ are the same or different and each is selected from the group consisting of hydrogen, straight or branched chain alkyl of 1 to 4 carbon atoms, alkoxy of 1 to 4 carbon atoms, alkylthio of 1 to 4 carbon atoms, trifluoromethyl, chlorine, bromine, nitro, cyano, amino, alkamoylamino of 1 to 4 carbon atoms, alkoxycarbonylamino of 1 to 4 carbon atoms in the alkoxy moiety, carboxy, alkoxycarbonyl of 1 to 4 carbon atoms in the alkoxy moiety, haloalkoxy of 1 to 4 carbon atoms in the alkoxy moiety, haloalkylthio of 1 to 4 carbon atoms in the alkyl moiety, carbamoyl, alkanoyl of 1 to 5 carbon atoms, haloalkanoyl of 1 to 4 carbon atoms, alkylsulphonyl of 1 to 4 carbon atoms, and haloalkylsulphonyl of 1 to 4 carbon atoms;

$R_{10}$ is hydrogen, straight chain alkyl of 1 to 12 carbon atoms, branched chain alkyl of 3 to 5 carbon atoms, ω-chloroalkyl of 1 to 6 carbon atoms, alkoxy of 1 to 6 carbon atoms, alkoxyalkyl of 2 to 6 carbon atoms, haloalkoxyalkyl of 2 to 6 carbon atoms, alkenyl of 2 to 4 carbon atoms, alkynyl of 2 to 4 carbon atoms, alkoxycarbonyl of 1 to 4 carbon atoms, (alkylthio)carbonyl of 1 to 4 carbon atoms, dialkylamino wherein the alkyl groups are the same and each alkyl group is of 1 to 4 carbon atoms, alkanoylamino of 1 to 5 carbon atoms, dilower alkanoylamino, polymethyleneimino, polymethyleneimino interrupted by oxygen, phenyl or halophenyl.

3. A composition according to claim 1 wherein
$R_1$, $R_2$, $R_3$, $R_4$, $R_5$, $R_6$, $R_7$, $R_8$ and $R_9$ are the same or different and each is selected from the group consisting of hydrogen, alkyl of 1 or 2 carbon atoms, alkoxy of 1 or 2 carbon atoms, alkylthio of 1 or 2 carbon atoms, trifluoromethyl, chlorine, bromine, nitro, cyano, amino, alkanoylamino of 1 or 2 carbon atoms, alkoxycarbonylamino of 1 or 2 carbon atoms, carboxy, alkoxycarbonyl of 1 or 2 carbon atoms, trifluoromethoxy, trifluoromethylthio, carbonyl, alkanoyl of 1 or 2 carbon atoms, trifluoroacetyl, alkylsulphonyl of 1 or 2 carbon atoms, and trifluoromethylsulphonyl; and $R_{10}$ is hydrogen, alkyl of 1 to 4 carbon atoms, alkoxy of 1 or 2 carbon atoms, alkoxyalkyl of 2 to 4 carbon atoms, trifluoromethoxymethyl, alkynyl of 2 or 3 carbon atoms, alkoxycarbonyl of 1 or 2 carbon atoms, (alkylthio)carbonyl of 1 or 2 carbon atoms, dimethylamino, diethylamino, phthalimido, succinimido, phenyl, chlorophenyl, or bromophenyl.

4. A composition according to claim 1 wherein $R_1$, $R_2$, $R_3$, $R_4$, $R_5$, $R_6$, $R_7$, $R_8$ and $R_9$ are the same or different and each is selected from the group consisting of hydrogen, alkyl of 1 or 2 carbon atoms, alkoxy of 1 or 2 carbon atoms, chlorine, bromine, nitro, cyano, trifluoromethyl, alkoxycarbonylamino of 1 or 2 carbon atoms, alkanoylamino of 1 to 2 carbon atoms, alkylsulphonyl of 1 or 2 carbon atoms and trifluoromethylsulphonyl;

$R_{10}$ is alkyl of 1 to 4 carbon atoms, amino or phthalimido; and $R_{11}$ is hydrogen.

5. A composition according to claim 4 wherein Y is oxygen.

6. A composition according to claim 1 wherein $R_1$, $R_4$, $R_9$ and $R_{11}$ are each hydrogen;

$R_2$ is hydrogen, alkyl of 1 or 2 carbon atoms, chlorine or bromine;

$R_3$ is hydrogen, alkyl of 1 or 2 carbon atoms, alkoxy of 1 or 2 carbon atoms, chlorine or bromine;

$R_5$ is alkyl of 1 or 2 carbon atoms, chlorine, bromine, nitro, cyano, trifluoromethyl, alkoxy, carbonylamino of 1 or 2 carbon atoms, alkanoylamino of 1 or 2 carbon atoms, alkylsulphonyl of 1 or 2 carbon atoms, or trifluoromethylsulphonyl;

$R_6$ is hydrogen, alkyl of 1 or 2 carbon atoms, chlorine, or bromine;

$R_7$ is hydrogen or alkyl of 1 or 2 carbon atoms;

$R_8$ is hydrogen, alkyl of 1 or 2 carbon atoms, chlorine, or bromine;

$R_{10}$ is alkyl of 1 to 4 carbon atoms, amino, or phthalimido; and

Y is oxygen.

7. A composition according to claim 1 wherein $R_1$ is hydrogen;

$R_2$ is hydrogen, methyl, or chlorine;

$R_3$ is hydrogen, methyl, methoxy, or chlorine;

$R_4$ is hydrogen;

$R_5$ is methyl, chlorine, nitro, cyano, trifluoromethyl, ethoxycarbonylamino, acetamido, methylsulphonyl, or trifluoromethylsulphonyl;

$R_6$ is hydrogen, methyl, or chlorine;

$R_7$ is hydrogen, or methyl;

$R_8$ is hydrogen, methyl, or chlorine;

$R_9$ is hydrogen;

$R_{10}$ is methyl, ethyl, propyl, butyl, amino, or phthalimido;

$R_{11}$ is hydrogen; and

Y is oxygen.

8. A composition according to claim 1 wherein $R_1$, $R_2$, $R_3$, $R_4$, $R_5$, $R_6$, $R_7$, $R_8$ and $R_9$ are the same or different and each is selected from the group consisting of hydrogen, alkyl of 1 to 4 carbon atoms, alkoxy of 1 or 2 carbon atoms, chlorine, bromine, nitro, cyano, trifluoromethyl, trifluoromethoxy, alkanoylamino of 1 or 2 carbon atoms, alkoxycarbonylamino of 1 or 2 carbon atoms, alkanoyl of 1 or 2 carbon atoms, or alkylsulphonyl of 1 or 2 carbon atoms;

$R_{10}$ is hydrogen, straight or branched chain alkyl of 1 to 4 carbon atoms, alkenyl of 2 or 3 carbon atoms, alkoxyalkyl of 2 to 5 carbon atoms, alkoxy of 1 or 2 carbon atoms, or phthalimido; and $R_{11}$ is hydrogen, or alkyl of 1 to 3 carbon atoms.

9. A composition according to claim 1 wherein $R_1$ is hydrogen, or alkyl of 1 or 2 carbon atoms;

$R_2$ is hydrogen, alkyl of 1 or 2 carbon atoms, chlorine, or bromine;

$R_3$ is hydrogen, alkyl of 1 or 2 carbon atoms, alkoxy of 1 or 2 carbon atoms, chlorine, or bromine;

$R_4$ is hydrogen, alkoxy of 1 or 2 carbon atoms, or cyano;

$R_5$ is hydrogen, straight or branched chain alkyl of 1 to 4 carbon atoms, chlorine, bromine, nitro, cyano, trifluoromethyl, trifluoromethoxy, alkanoylamino of 1 or 2 carbon atoms, alkoxycarbonyl of 1 or 2 carbon atoms, alkanoyl of 1 to 2 carbon atoms, or alkylsulphonyl of 1 or 2 carbon atoms;

$R_6$ is hydrogen, alkyl of 1 or 2 carbon atoms, alkoxy of 1 or 2 carbon atoms, chlorine, bromine, or trifluoromethyl;

$R_7$ is hydrogen, alkyl of 1 or 2 carbon atoms, alkoxy of 1 or 2 carbon atoms, chlorine, or bromine;

$R_8$ is hydrogen, alkyl of 1 to or 2 carbon atoms, chlorine, or bromine;

$R_9$ is hydrogen;

$R_{10}$ is hydrogen, straight or branched chain alkyl of 1 to 4 carbon atoms, alkenyl of 2 or 3 carbon atoms, alkoxyalkyl of 2 to 5 carbon atoms, alkoxy of 1 or 2 carbon atoms, or phthalimido; and $R_{11}$ is hydrogen, or alkyl of 1 to 3 carbon atoms.

10. A composition according to claim 1 wherein $R_1$ is hydrogen, or methyl;

$R_2$ is hydrogen, methyl, or chlorine;

$R_3$ is hydrogen, methyl, ethyl, methoxy, or chlorine;

$R_4$ is hydrogen, ethoxy, or cyano;

$R_5$ is hydrogen, methyl, tert.-butyl, chlorine, bromine, nitro, cyano, trifluoromethyl, trifluoromethoxy, acetamido, ethoxycarbonylamino, acetyl, or methylsulphonyl;

$R_6$ is hydrogen, methyl, methoxy, chlorine, or trifluoromethyl;

$R_7$ is hydrogen, methyl, methoxy, or chlorine;

$R_8$ is hydrogen, methyl, or chlorine;

$R_9$ is hydrogen;

$R_{10}$ is hydrogen, methyl, ethyl, n-propyl, i-propyl, tert.-butyl, allyl, methoxyethyl, methoxypropyl, ethoxypropyl, methoxy, ethoxy, or phthalimido; and $R_{11}$ is hydrogen, or propyl.

11. The composition according to claim 1 wherein the compound is 1-[4-(4'-ethoxycarbonylaminophenylthio)-phenyl]-3-methyl-1,3,5-triazine-2,4,6(1H,3H,5H)-trione.

12. The composition according to claim 1 wherein the compound is 1-[4-(4'-nitrophenylthio)-phenyl]-3-methyl-1,3,5-triazine-2,4,6(1H,3H,5H)-trione.

13. The composition according to claim 1 wherein the compound is 1-[4-(4'-nitrophenylthio)-phenyl]-3-ethyl-1,3,5,-triazine-2,4,6(1H,3H,5H)-trione.

14. The composition according to claim 1 wherein the compound is 1-[4-(4'-nitrophenylthio)-phenyl]-3-propyl-1,3,5-triazine-2,4,6(1H,3H,5H)-trione.

15. The composition according to claim 1 wherein the compound is 1-[4-(4'-cyanophenylthio)-phenyl]-3-methyl-1,3,5-triazine-2,4,6(1H,3H,5H)-trione.

16. The composition according to claim 1 wherein the compound is 1-[4-(4'-chlorophenylsulphonyl)-phenyl]-3-methyl-1,3,5-triazine-2,4,6(1H,3H,5H)-trione.

17. A composition according to claim 1 in oral administration form.

18. A composition according to claim 1 in parenteral administration form.

19. A composition according to claim 1 in topical application form.

20. An animal feedstuff which comprises 25 to 5,000 ppm of a compound of the formula:

$$\text{[structural formula]}$$

or a pharmaceutically acceptable nontoxic salt thereof wherein $R_1$, $R_2$, $R_3$, $R_4$, $R_5$, $R_6$, $R_7$, $R_8$ and $R_9$ are the same or different and each is selected from the group consisting of hydrogen, straight or branched chain lower alkyl, halo lower alkyl, lower alkoxy, halo lower alkoxy, lower alkylthio, halo lower alkylthio, halogen, nitro, cyano, amino, lower alkanoylamino, lower alkoxycarbonylamino, carboxy, lower alkoxycarbonyl, carbamoyl, lower alkanoyl, halo lower alkanoyl, lower alkylsulphinyl, lower alkylsulphonyl, halo lower alkylsulphonyl, and sulphamoyl;

$R_{10}$ is hydrogen, straight or branched chain lower alkyl, cycloalkyl of 3 to 7 carbon atoms, halo lower alkyl, lower alkoxy, lower alkoxy lower alkyl, halo lower alkoxy lower alkyl, lower alkylthio lower alkyl, halo lower alkylthio lower alkyl, lower alkenyl, lower alkynyl, lower alkoxycarbonyl, (lower alkylthio)carbonyl, (lower alkylthio)thiocarbonyl, lower alkanoylamino, succinimido, phthalimido, amino, dilower alkylamino, benzyl, phenyl, or benzyl or phenyl substituted by halogen;

$R_{11}$ is hydrogen or lower alkyl;

X is sulphur, sulphinyl or sulphonyl; and

Y is oxygen or sulphur;

in combination with an edible nutritious material.

21. A feedstuff according to claim 20 wherein the compound is present in an amount of 50 to 250 ppm.

22. Coccidiocidal drinking water for animals which comprises 25 to 5,000 ppm of a compound of the formula:

$$\text{[structural formula]}$$

or a pharmaceutically acceptable nontoxic salt thereof wherein $R_1$, $R_2$, $R_3$, $R_4$, $R_5$, $R_6$, $R_7$, $R_8$ and $R_9$ are the same or different and each is selected from the group consisting of hydrogen, straight or branched chain lower alkyl, halo lower alkyl, lower alkoxy, halo lower alkoxy, lower alkylthio, halo lower alkylthio, halogen, nitro, cyano, amino, lower alkanoylamino, lower alkoxycarbonylamino, carboxy, lower alkoxycarbonyl, carbamoyl, lower alkanoyl, halo lower alkanoyl, lower alkylsulphinyl, lower alkylsulphonyl, halo lower alkylsulphonyl, and sulphamoyl;

$R_{10}$ is hydrogen, straight or branched chain lower alkyl, cycloalkyl of 3 to 7 carbon atoms, halo lower alkyl, lower alkoxy, lower alkoxy lower alkyl, halo lower alkoxy lower alkyl, lower alkylthio lower alkyl, halo lower alkylthio lower alkyl, lower alkenyl, lower alkynyl, lower alkoxycarbonyl, (lower alkylthio)carbonyl, (lower alkylthio)thiocarbonyl, lower alkanoylamino, succinimido, phthalimido, amino, dilower alkylamino, benzyl, phenyl, or benzyl or phenyl substituted by halogen;

$R_{11}$ is hydrogen or lower alkyl;

X is sulphur, sulphinyl or sulphonyl; and

Y is oxygen or sulphur;

dissolved in water suitable for drinking by animals.

23. An animal concentrate or premix which comprises 1 to 30% by weight of a compound of the formula:

$$\text{[structural formula]}$$

or a pharmaceutically acceptable nontoxic salt thereof wherein $R_1$, $R_2$, $R_3$, $R_4$, $R_5$, $R_6$, $R_7$, $R_8$ and $R_9$ are the same or different and each is selected from the group consisting of hydrogen, straight or branched chain lower alkyl, halo lower alkyl, lower alkoxy, halo lower alkoxy, lower alkylthio, halo lower alkylthio, halogen, nitro, cyano, amino, lower alkanoylamino, lower alkoxycarbonylamino, carboxy, lower alkoxycarbonyl, carbamoyl, lower alkanoyl, halo lower alkanoyl, lower alkylsulphinyl, lower alkylsulphonyl, halo lower alkylsulphonyl, and sulphamoyl;

$R_{10}$ is hydrogen, straight or branched chain lower alkyl, cycloalkyl of 3 to 7 carbon atoms, halo lower alkyl, lower alkoxy, lower alkoxy lower alkyl, halo lower alkoxy lower alkyl, lower alkylthio lower alkyl, halo lower alkylthio lower alkyl, lower alkenyl, lower alkynyl, lower alkoxycarbonyl, (lower alkylthio)carbonyl, (lower alkylthio)thiocarbonyl, lower alkanoylamino, succinimido, phthalimido, amino, dilower alkylamino, benzyl, phenyl, or benzyl or phenyl substituted by halogen;

$R_{11}$ is hydrogen or lower alkyl;

X is sulphur, sulphinyl or sulphonyl; and

Y is oxygen or sulphur;

in combination with an edible organic or inorganic carrier.

24. A concentrate or premix according to claim 23 wherein the compound is present in the amount of 10 to 20% by weight.

25. A method of treating coccidiosis or effecting prophylaxis against coccidiosis in humans and animals which comprises administering to such human or animal an effective amount of a compound of the formula:

[Structural formula: a disubstituted benzene (R$_3$–R$_7$) linked by X to another benzene (R$_1$, R$_2$, R$_8$, R$_9$) which is attached to an N of a ring containing C=Y, N-R$_{10}$, C=O, and R$_{11}$.]

or a pharmaceutically acceptable nontoxic salt thereof wherein $R_1$, $R_2$, $R_3$, $R_4$, $R_5$, $R_6$, $R_7$, $R_8$ and $R_9$ are the same or different and each is selected from the group consisting of hydrogen, straight or branched chain lower alkyl, halo lower alkyl, lower alkoxy, halo lower alkoxy, lower alkylthio, halo lower alkylthio, halogen, nitro, cyano, amino, lower alkanoylamino, lower alkoxycarbonylamino, carboxy, lower alkoxycarbonyl, carbamoyl, lower alkanoyl, halo lower alkanoyl, lower alkylsulphinyl, lower alkylsulphonyl, halo lower alkylsulphonyl, and sulphamoyl;

$R_{10}$ is hydrogen, straight or branched chain lower alkyl, cycloalkyl of 3 to 7 carbon atoms, halo lower alkyl, lower alkoxy, lower alkoxy lower alkyl, halo lower alkoxy lower alkyl, lower alkylthio lower alkyl, halo lower alkylthio lower alkyl, lower alkenyl, lower alkynyl, lower alkoxycarbonyl, (lower alkylthio)carbonyl, (lower alkylthio)thiocarbonyl, lower alkanoylamino, succinimido, phthalimido, amino, dilower alkylamino, benzyl, phenyl, or benzyl or phenyl substituted by halogen;

$R_{11}$ is hydrogen or lower alkyl;

X is sulphur, sulphinyl or sulphonyl; and

Y is oxygen or sulphur.

26. A method according to claim 25 wherein $R_1$, $R_2$, $R_3$, $R_4$, $R_5$, $R_6$, $R_7$, $R_8$ and $R_9$ are the same or different and each is selected from the group consisting of hydrogen, straight or branched chain alkyl of 1 to 4 carbon atoms, alkoxy of 1 to 4 carbon atoms, alkylthio of 1 to 4 carbon atoms, trifluoromethyl, chlorine, bromine, nitro, cyano, amino, alkanoylamino of 1 to 4 carbon atoms, alkoxycarbonylamino of 1 to 4 carbon atoms in the alkoxy moiety, carboxy, alkoxycarbonyl of 1 to 4 carbon atoms in the alkoxy moiety, haloalkoxy of 1 to 4 carbon atoms in the alkoxy moiety, haloalkylthio of 1 to 4 carbon atoms in the alkyl moiety, carbamoyl, alkanoyl of 1 to 5 carbon atoms, halo alkanoyl of 1 to 4 carbon atoms, alkylsulphonyl of 1 to 4 carbon atoms and haloalkylsulphonyl of 1 to 4 carbon atoms;

$R_{10}$ is hydrogen, straight chain alkyl of 1 to 12 carbon atoms, branched chain alkyl of 3 to 5 carbon atoms, -chloroalkyl of 1 to 6 carbon atoms, alkoxy of 1 to 6 carbon atoms, alkoxyalkyl of 2 to 6 carbon atoms, haloalkoxyalkyl of 2 to 6 carbon atoms, alkenyl of 2 to 4 carbon atoms, alkynyl of 2 to 4 carbon atoms, alkoxycarbonyl of 1 to 4 carbon atoms, (alkylthio)carbonyl of 1 to 4 carbon atoms, dialkylamino wherein the alkyl groups are the same and each alkyl group is of 1 to 4 carbon atoms, alkanoylamino of 1 to 5 carbon atoms, succinimido, phthalimido, phenyl or halophenyl.

27. A method according to claim 25 wherein $R_1$, $R_2$, $R_3$, $R_4$, $R_5$, $R_6$, $R_7$, $R_8$ and $R_9$ are the same or different and each is selected from the group consisting of hydrogen, alkyl of 1 or 2 carbon atoms, alkoxy of 1 or 2 carbon atoms, alkylthio of 1 or 2 carbon atoms, trifluoromethyl, chlorine, bromine, nitro, cyano, amino, alkanoylamino of 1 or 2 carbon atoms, alkoxycarbonylamino of 1 or 2 carbon atoms, carboxy, alkoxycarbonyl of 1 or 2 carbon atoms, trifluoromethoxy, trifluoromethylthio, carbonyl, alkanoyl of 1 or 2 carbon atoms, trifluoroacetyl, alkylsulphonyl of 1 or 2 carbon atoms, and trifluoromethylsulphonyl; and $R_{10}$ is hydrogen, alkyl of 1 to 4 carbon atoms, alkoxy of 1 or 2 carbon atoms, alkoxyalkyl of 2 to 4 carbon atoms, trifluoromethoxymethyl, alkynyl of 2 or 3 carbon atoms, alkoxycarbonyl of 1 or 2 carbon atoms, (alkylthio)carbonyl of 1 or 2 carbon atoms, dimethylamino, diethylamino, phthalimido, succinimido, phenyl, chlorophenyl, or bromophenyl.

28. A method according to claim 25 wherein $R_1$, $R_2$, $R_3$, $R_4$, $R_5$, $R_6$, $R_7$, $R_8$ and $R_9$ are the same or different and each is selected from the group consisting of hydrogen, alkyl of 1 or 2 carbon atoms, alkoxy of 1 or 2 carbon atoms, chlorine, bromine, nitro, cyano, trifluoromethyl, alkoxycarbonylamino of 1 or 2 carbon atoms, alkanoylamino of 1 or 2 carbon atoms, alkylsulphonyl of 1 or 2 carbon atoms and trifluoromethylsulphonyl;

$R_{10}$ is alkyl of 1 to 4 carbon atoms, amino or phthalimido; and $R_{11}$ is hydrogen.

29. A method according to claim 28 wherein Y is oxygen.

30. A method according to claim 25 wherein $R_1$, $R_4$, $R_9$ and $R_{11}$ are each hydrogen;

$R_2$ is hydrogen, alkyl of 1 or 2 carbon atoms, chlorine or bromine;

$R_3$ is hydrogen, alkyl of 1 or 2 carbon atoms, alkoxy of 1 or 2 carbon atoms, chlorine or bromine;

$R_5$ is alkyl of 1 or 2 carbon atoms, chlorine, bromine, nitro, cyano, trifluoromethyl, alkoxy, carbonylamino of 1 or 2 carbon atoms, alkanoylamino of 1 or 2 carbon atoms, alkylsulphonyl of 1 or 2 carbon atoms, or trifluoromethylsulphonyl;

$R_6$ is hydrogen, alkyl of 1 or 2 carbon atoms, chlorine, or bromine;

$R_7$ is hydrogen or alkyl of 1 or 2 carbon atoms;

$R_8$ is hydrogen, alkyl of 1 or 2 carbon atoms, chlorine, or bromine;

$R_{10}$ is alkyl of 1 to 4 carbon atoms, amino, or phthalimido; and

Y is oxygen.

31. A method according to claim 25 wherein $R_1$ is hydrogen;
$R_2$ is hydrogen, methyl, or chlorine;
$R_3$ is hydrogen, methyl, methoxy, or chlorine;
$R_4$ is hydrogen;
$R_5$ is methyl, chlorine, nitro, cyano, trifluoromethyl, ethoxycarbonylamino, acetamido, methylsulphonyl, or trifluoromethylsulphonyl;
$R_6$ is hydrogen, methyl, or chlorine;
$R_7$ is hydrogen, or methyl;
$R_8$ is hydrogen, methyl, or chlorine;
$R_9$ is hydrogen;
$R_{10}$ is methyl, ethyl, propyl, butyl, amino, or phthalimido;
$R_{11}$ is hydrogen; and
Y is oxygen.

32. A method according to claim 25 wherein $R_1$, $R_2$, $R_3$, $R_4$, $R_5$, $R_6$, $R_7$, $R_8$ and $R_9$ are the same or different and each is selected from the group consisting of hydrogen, alkyl of 1 to 4 carbon atoms, alkoxy of 1 or 2 carbon atoms, chlorine, bromine, nitro, cyano, trifluoromethyl, trifluoromethoxy, acylamino of 1 or 2 carbon atoms, alkoxycarbonylamino of 1 or 2 carbon atoms, alkanoyl of 1 or 2 carbon atoms, or alkylsulphonyl of 1 or 2 carbon atoms;

$R_{10}$ is hydrogen, straight or branched chain alkyl of 1 to 4 carbon atoms, alkenyl of 2 or 3 carbon atoms, alkoxyalkyl of 2 to 5 carbon atoms, alkoxy of 1 or 2 carbon atoms, or phthalimido; and $R_{11}$ is hydrogen, or alkyl of 1 to 3 carbon atoms.

33. A method according to claim 25 wherein
$R_1$ is hydrogen, or alkyl of 1 or 2 carbon atoms;
$R_2$ is hydrogen, alkyl of 1 or 2 carbon atoms, chlorine, or bromine;
$R_3$ is hydrogen, alkyl of 1 or 2 carbon atoms, alkoxy of 1 or 2 carbon atoms, chlorine, or bromine;
$R_4$ is hydrogen, alkoxy of 1 or 2 carbon atoms, or cyano;
$R_5$ is hydrogen, straight or branched chain alkyl of 1 to 4 carbon atoms, chlorine, bromine, nitro, cyano, trifluoromethyl, trifluoromethoxy, acylamino of 1 or 2 carbon atoms, alkoxycarbonyl of 1 or 2 carbon atoms, alkanoyl of 1 or 2 carbon atoms, or alkylsulphonyl of 1 or 2 carbon atoms;
$R_6$ is hydrogen, alkyl of 1 or 2 carbon atoms, alkoxy of 1 or 2 carbon atoms, chlorine, bromine, or trifluoromethyl;
$R_7$ is hydrogen, alkyl of 1 or 2 carbon atoms, alkoxy of 1 or 2 carbon atoms, chlorine, or bromine;
$R_8$ is hydrogen, alkyl of 1 or 2 carbon atoms, chlorine, or bromine;
$R_9$ is hydrogen;
$R_{10}$ is hydrogen, straight or branched chain alkyl of 1 to 4 carbon atoms, alkenyl of 2 or 3 carbon atoms, alkoxyalkyl of 2 to 5 carbon atoms, alkoxy of 1 or 2 carbon atoms, or phthalimido; and
$R_{11}$ is hydrogen, or alkyl of 1 to 3 carbon atoms.

34. A method according to claim 25 wherein
$R_1$ is hydrogen, or methyl;
$R_2$ is hydrogen, methyl, or chlorine;
$R_3$ is hydrogen, methyl, ethyl, methoxy, or chlorine;
$R_4$ is hydrogen, ethoxy, or cyano;
$R_5$ is hydrogen, methyl, tert.-butyl, chlorine, bromine, nitro, cyano, trifluoromethyl, trifluoromethoxy, acetamido, ethoxycarbonylamino, acetyl, or methylsulphonyl;
$R_6$ is hydrogen, methyl, methoxy, chlorine, or trifluoromethyl;
$R_7$ is hydrogen, methyl, methoxy, or chlorine;
$R_8$ is hydrogen, methyl, or chlorine;
$R_9$ is hydrogen;
$R_{10}$ is hydrogen, methyl, ethyl, n-propyl, i-propyl, tert.-butyl, allyl, methoxyethyl, methoxypropyl, ethoxypropyl, methoxy, ethoxy, or phthalimido; and
$R_{11}$ is hydrogen, or propyl.

35. The method according to claim 25 wherein the compound is 1-[4-(4'-ethoxycarbonylamino-phenylthio)-phenyl]-3-methyl-1,3,5-triazine-2,4,6(1H,3H,5H)-trione.

36. The method according to claim 25 wherein the compound is 1-[4-(4'-nitro-phenylthio)-phenyl]-3-methyl-1,3,5-triazine-2,4,6(1H,3H,5H)-trione.

37. The method according to claim 25 wherein the compound is 1-[4-(4'-nitro-phenylthio)-phenyl]-3-ethyl-1,3,5-triazine-2,4,6-(1H,3H,5H)-trione.

38. The method according to claim 25 wherein the compound is 1-[4-(4'-nitro-phenylthio)-phenyl]-3-propyl-1,3,5-triazine-2,4,6(1H,3H,5H)-trione.

39. The method according to claim 25 wherein the compound is 1-[4-(4'-cyano-phenylthio)-phenyl]-3-methyl-1,3,5-triazine-2,4,6-(1H,3H,5H)-trione.

40. The method according to claim 25 wherein the compound is 1-([4-(4'-chloro-phenylsulphonyl)-phenyl]-3-methyl-1,3,5-triazine-2,4,6-(1H,3H,5H)-trione.

41. A method according to claim 25 wherein the administration is oral.

42. A method according to claim 25 wherein the administration is parenteral.

43. A method according to claim 25 wherein the administration is by topical application.

* * * * *